(12) United States Patent
Arneson et al.

(10) Patent No.: US 9,351,632 B2
(45) Date of Patent: May 31, 2016

(54) DISPLAYING IMAGE DATA FROM A SCANNER CAPSULE

(71) Applicant: Innurvation, Inc., Columbia, MD (US)

(72) Inventors: Michael Arneson, Finksburg, MD (US); William R. Bandy, Gambrills, MD (US); Kevin J. Powell, Annapolis, MD (US); Kenneth E. Salsman, Pleasanton, CA (US); Devon Tirpack, Chester Springs, PA (US)

(73) Assignee: INNURVATION, INC., Glen Burnie, MD (US)

( * ) Notice: Subject to any disclaimer, the term of this patent is extended or adjusted under 35 U.S.C. 154(b) by 0 days.

(21) Appl. No.: 14/072,997

(22) Filed: Nov. 6, 2013

(65) Prior Publication Data

US 2014/0249373 A1    Sep. 4, 2014

Related U.S. Application Data

(63) Continuation of application No. 12/500,232, filed on Jul. 9, 2009, now Pat. No. 8,617,058.

(60) Provisional application No. 61/079,342, filed on Jul. 9, 2008.

(51) Int. Cl.
*A61B 1/06* (2006.01)
*A61B 1/04* (2006.01)
*A61B 1/00* (2006.01)

(52) U.S. Cl.
CPC ............. *A61B 1/041* (2013.01); *A61B 1/00009* (2013.01); *A61B 1/00041* (2013.01)

(58) Field of Classification Search
CPC ... A61B 1/041; A61B 1/0009; A61B 1/00041
USPC .......................................................... 600/160
See application file for complete search history.

(56) References Cited

U.S. PATENT DOCUMENTS 2,788,390 A    4/1957 Sheldon
2,987,960 A    6/1961 Sheldon
(Continued)

FOREIGN PATENT DOCUMENTS

EP    1 326 432 A2    7/2003
EP    1 492 352 A2    12/2004
(Continued)

OTHER PUBLICATIONS

European Patent Office. PCT Notification of Transmittal of the International Search Report and the Written Opinion of the International Searching Authority, or the Declaration. International Application No. PCT/US2009/0040000. International Filing Date: Sep. 7, 2009 Applicant: Innurvation, Inc. Form PCT/ISA/220. Mailing Date: Mar. 29, 2010. 3 pages.
(Continued)

*Primary Examiner* — Rodney Fuller
(74) *Attorney, Agent, or Firm* — Sterne, Kessler, Goldstein & Fox P.L.L.C.

(57) ABSTRACT

An ingestible image scanning pill captures high resolution images of the GI tract as it passes through. Images communicated externally have exact location determination. Image processing software discards duplicate information and stitches images together, line scan by line scan, to replicate a complete GI tract as if it were stretched out in a straight line. A fully linear image is displayed to a medical professional as if the GI tract had been stretched in a straight line, cut open, laid flat out on a bench for viewing—all without making any incisions in a live patient.

14 Claims, 21 Drawing Sheets

(56) References Cited

U.S. PATENT DOCUMENTS

| | | |
|---|---|---|
| 3,329,074 A | 7/1967 | Gosselin |
| 3,608,547 A | 9/1971 | Sato et al. |
| 3,730,175 A | 5/1973 | Fukami et al. |
| 4,987,897 A | 1/1991 | Funke |
| 5,010,412 A | 4/1991 | Garriss |
| 5,131,398 A | 7/1992 | Alfano et al. |
| 5,251,326 A | 10/1993 | Silverman |
| 5,265,603 A | 11/1993 | Hudrlik |
| 5,267,033 A | 11/1993 | Hoshino |
| 5,279,607 A | 1/1994 | Schentag et al. |
| 5,329,498 A | 7/1994 | Greenstein |
| 5,395,366 A | 3/1995 | D'Andrea et al. |
| 5,522,865 A | 6/1996 | Schulman et al. |
| 5,541,954 A | 7/1996 | Emi |
| 5,559,757 A | 9/1996 | Catipovic et al. |
| 5,604,531 A | 2/1997 | Iddan et al. |
| 5,741,311 A | 4/1998 | Mc Venes et al. |
| 5,744,898 A | 4/1998 | Smith et al. |
| 5,796,827 A | 8/1998 | Coppersmith et al. |
| 5,833,603 A | 11/1998 | Kovacs et al. |
| 5,984,875 A | 11/1999 | Brune |
| 5,993,378 A | 11/1999 | Lemelson |
| 5,995,136 A | 11/1999 | Hattori et al. |
| 5,999,131 A | 12/1999 | Sullivan |
| 6,076,016 A | 6/2000 | Feierbach |
| 6,104,913 A | 8/2000 | McAllister |
| 6,115,636 A | 9/2000 | Ryan |
| 6,172,789 B1 | 1/2001 | Kino et al. |
| 6,198,324 B1 | 3/2001 | Schober |
| 6,198,965 B1 | 3/2001 | Penner et al. |
| 6,211,799 B1 | 4/2001 | Post et al. |
| 6,239,724 B1 | 5/2001 | Doron et al. |
| 6,240,312 B1 | 5/2001 | Alfano et al. |
| 6,252,448 B1 | 6/2001 | Schober |
| 6,269,379 B1 | 7/2001 | Hiyama et al. |
| 6,294,775 B1 | 9/2001 | Seibel et al. |
| 6,297,668 B1 | 10/2001 | Schober |
| 6,333,656 B1 | 12/2001 | Schober |
| 6,380,858 B1 | 4/2002 | Yarin et al. |
| D457,236 S | 5/2002 | Meron et al. |
| D457,621 S | 5/2002 | Meron et al. |
| D457,948 S | 5/2002 | Meron et al. |
| 6,431,175 B1 | 8/2002 | Penner et al. |
| D464,425 S | 10/2002 | Meron et al. |
| 6,484,818 B2 | 11/2002 | Alft et al. |
| 6,486,588 B2 | 11/2002 | Doron et al. |
| 6,504,286 B1 | 1/2003 | Porat et al. |
| D469,864 S | 2/2003 | Meron et al. |
| 6,563,105 B2 | 5/2003 | Seibel et al. |
| 6,580,858 B2 | 6/2003 | Chen et al. |
| 6,584,348 B2 | 6/2003 | Glukhovsky |
| 6,597,320 B2 | 7/2003 | Maeda et al. |
| 6,607,301 B1 | 8/2003 | Glukhovsky et al. |
| 6,628,989 B1 | 9/2003 | Penner et al. |
| 6,702,755 B1 | 3/2004 | Stasz et al. |
| 6,709,387 B1 | 3/2004 | Glukhovsky et al. |
| 6,720,709 B2 | 4/2004 | Porat et al. |
| D492,403 S | 6/2004 | Iddan et al. |
| 6,754,472 B1 | 6/2004 | Williams et al. |
| 6,764,446 B2 | 7/2004 | Wolinsky et al. |
| 6,784,826 B2 | 8/2004 | Kane et al. |
| 6,836,377 B1 | 12/2004 | Kislev et al. |
| 6,845,190 B1 | 1/2005 | Smithwick et al. |
| 6,847,844 B2 | 1/2005 | Sun et al. |
| 6,855,111 B2 | 2/2005 | Yokoi et al. |
| 6,856,712 B2 | 2/2005 | Fauver et al. |
| 6,867,753 B2 | 3/2005 | Chinthammit et al. |
| 6,904,308 B2 | 6/2005 | Frisch et al. |
| 6,918,872 B2 | 7/2005 | Yokoi et al. |
| 6,934,093 B2 | 8/2005 | Kislev et al. |
| 6,934,573 B1 | 8/2005 | Glukhovsky et al. |
| 6,936,003 B2 | 8/2005 | Iddan |
| D510,139 S | 9/2005 | Gilad et al. |
| 6,939,290 B2 | 9/2005 | Iddan |
| 6,939,292 B2 | 9/2005 | Mizuno |
| 6,944,316 B2 | 9/2005 | Glukhovsky et al. |
| 6,950,690 B1 | 9/2005 | Meron et al. |
| 6,958,034 B2 | 10/2005 | Iddan |
| D512,150 S | 11/2005 | Iddan et al. |
| 6,975,898 B2 | 12/2005 | Seibel |
| 6,984,205 B2 | 1/2006 | Gazdzinski |
| 7,009,634 B2 | 3/2006 | Iddan et al. |
| 7,022,066 B2 | 4/2006 | Yokoi et al. |
| 7,022,067 B2 | 4/2006 | Glukhovsky et al. |
| 7,024,248 B2 | 4/2006 | Penner et al. |
| 7,039,453 B2 | 5/2006 | Mullick et al. |
| 7,060,094 B2 | 6/2006 | Shahinpoor et al. |
| 7,095,905 B1 * | 8/2006 | Peterson ............... 382/284 |
| 7,109,859 B2 | 9/2006 | Peeters |
| 7,118,529 B2 | 10/2006 | Glukhovsky et al. |
| 7,118,531 B2 | 10/2006 | Krill |
| 7,119,814 B2 | 10/2006 | Meron et al. |
| 7,122,001 B2 | 10/2006 | Uchiyama et al. |
| 7,140,766 B2 | 11/2006 | Glukhovsky et al. |
| 7,160,258 B2 | 1/2007 | Imran et al. |
| 7,161,164 B2 | 1/2007 | Glukhovsky |
| 7,195,588 B2 | 3/2007 | Homan et al. |
| 7,200,253 B2 | 4/2007 | Glukhovsky et al. |
| D543,272 S | 5/2007 | Gilad et al. |
| 7,251,383 B2 | 7/2007 | Iddan |
| 7,295,226 B1 | 11/2007 | Meron et al. |
| 7,307,544 B2 | 12/2007 | Kim et al. |
| 7,316,647 B2 | 1/2008 | Kimoto et al. |
| 7,319,896 B2 | 1/2008 | Konno |
| 7,321,673 B2 | 1/2008 | Watai et al. |
| 7,327,525 B2 | 2/2008 | Kislev et al. |
| 7,336,833 B2 | 2/2008 | Horn |
| 7,339,622 B2 | 3/2008 | Yokokawa |
| 7,343,036 B2 | 3/2008 | Kleen et al. |
| 7,347,817 B2 | 3/2008 | Glukhovsky et al. |
| 7,348,571 B2 | 3/2008 | Ue |
| 7,354,397 B2 | 4/2008 | Fujita et al. |
| 7,356,255 B2 | 4/2008 | Nonaka |
| 7,452,338 B2 | 11/2008 | Taniguchi |
| 7,488,287 B2 | 2/2009 | Kawashima |
| 7,511,733 B2 | 3/2009 | Takizawa et al. |
| 7,559,890 B2 | 7/2009 | Wallace et al. |
| 7,565,019 B2 * | 7/2009 | Dong et al. ............... 382/236 |
| 7,646,932 B1 * | 1/2010 | Peterson ............... 382/284 |
| 7,647,090 B1 | 1/2010 | Frisch et al. |
| 7,664,174 B2 | 2/2010 | Avni et al. |
| 7,744,528 B2 | 6/2010 | Wallace et al. |
| 7,775,977 B2 | 8/2010 | Kawashima et al. |
| 7,805,178 B1 | 9/2010 | Gat |
| 7,833,151 B2 | 11/2010 | Khait et al. |
| 7,841,981 B2 | 11/2010 | Kawano et al. |
| 7,866,322 B2 | 1/2011 | Iddan |
| 7,872,667 B2 | 1/2011 | Iddan et al. |
| 7,931,584 B2 | 4/2011 | Akagi et al. |
| 7,940,603 B2 | 5/2011 | Adachi et al. |
| 7,998,067 B2 | 8/2011 | Kimoto et al. |
| 8,026,651 B2 | 9/2011 | Wakabayashi et al. |
| 8,036,731 B2 | 10/2011 | Kimchy et al. |
| 8,047,995 B2 | 11/2011 | Wakabayashi et al. |
| 8,118,774 B2 | 2/2012 | Dann et al. |
| 8,125,516 B2 | 2/2012 | Iddan et al. |
| 8,512,241 B2 | 8/2013 | Bandy et al. |
| 8,617,058 B2 | 12/2013 | Arneson et al. |
| 8,636,653 B2 * | 1/2014 | Wilson ............... 600/160 |
| 2001/0035902 A1 | 11/2001 | Iddan et al. |
| 2002/0032366 A1 | 3/2002 | Iddan et al. |
| 2002/0109774 A1 | 8/2002 | Meron et al. |
| 2002/0138009 A1 | 9/2002 | Brockway et al. |
| 2002/0158976 A1 | 10/2002 | Vni et al. |
| 2002/0165592 A1 | 11/2002 | Glukhovsky et al. |
| 2002/0168144 A1 | 11/2002 | Chen et al. |
| 2002/0173718 A1 | 11/2002 | Frisch et al. |
| 2002/0177779 A1 | 11/2002 | Adler et al. |
| 2002/0193669 A1 | 12/2002 | Glukhovsky |
| 2002/0198470 A1 | 12/2002 | Imran |
| 2003/0013370 A1 | 1/2003 | Glukhovsky |
| 2003/0018280 A1 | 1/2003 | Lewkowicz et al. |
| 2003/0020810 A1 | 1/2003 | Takizawa et al. |
| 2003/0028078 A1 | 2/2003 | Glukhovsky |

(56) References Cited

U.S. PATENT DOCUMENTS

| | | | |
|---|---|---|---|
| 2003/0040685 A1 | 2/2003 | Lewkowicz et al. | |
| 2003/0043263 A1 | 3/2003 | Glukhovsky et al. | |
| 2003/0045790 A1 | 3/2003 | Lewkowicz et al. | |
| 2003/0077223 A1 | 4/2003 | Glukhovsky et al. | |
| 2003/0114742 A1 | 6/2003 | Lewkowicz et al. | |
| 2003/0117491 A1 | 6/2003 | Avni et al. | |
| 2003/0139661 A1 | 7/2003 | Kimchy et al. | |
| 2003/0174208 A1 | 9/2003 | Glukhovsky et al. | |
| 2003/0195415 A1 | 10/2003 | Iddan | |
| 2004/0027500 A1 | 2/2004 | Davidson et al. | |
| 2004/0032187 A1 | 2/2004 | Penner et al. | |
| 2004/0073087 A1 | 4/2004 | Glukhovsky et al. | |
| 2004/0109488 A1 | 6/2004 | Glukhovsky et al. | |
| 2004/0114856 A1 | 6/2004 | Kubby et al. | |
| 2004/0122315 A1 | 6/2004 | Krill | |
| 2004/0127785 A1 | 7/2004 | Davidson et al. | |
| 2004/0138532 A1 | 7/2004 | Glukhovsky | |
| 2004/0171915 A1 | 9/2004 | Glukhovsky et al. | |
| 2004/0176685 A1 | 9/2004 | Takizawa et al. | |
| 2004/0181155 A1 | 9/2004 | Glukhovsky | |
| 2004/0199054 A1 | 10/2004 | Wakefield | |
| 2004/0199061 A1 | 10/2004 | Glukhovsky | |
| 2004/0199222 A1 | 10/2004 | Sun et al. | |
| 2004/0202339 A1 | 10/2004 | O'Brien, Jr. et al. | |
| 2004/0204744 A1 | 10/2004 | Penner et al. | |
| 2004/0210105 A1 | 10/2004 | Hale et al. | |
| 2004/0236182 A1 | 11/2004 | Iddan et al. | |
| 2004/0240077 A1 | 12/2004 | Kislev et al. | |
| 2004/0257384 A1* | 12/2004 | Park et al. | 345/646 |
| 2004/0258328 A1 | 12/2004 | Adler | |
| 2005/0025368 A1 | 2/2005 | Glukhovsky | |
| 2005/0065441 A1 | 3/2005 | Glukhovsky | |
| 2005/0068416 A1 | 3/2005 | Glukhovsky et al. | |
| 2005/0075555 A1 | 4/2005 | Glukhovsky et al. | |
| 2005/0088299 A1 | 4/2005 | Bandy et al. | |
| 2005/0096526 A1 | 5/2005 | Reinschke | |
| 2005/0110881 A1 | 5/2005 | Glukhovsky et al. | |
| 2005/0119577 A1 | 6/2005 | Taniguchi | |
| 2005/0141624 A1 | 6/2005 | Lakshmipathi et al. | |
| 2005/0143644 A1 | 6/2005 | Gilad et al. | |
| 2005/0148816 A1 | 7/2005 | Glukhovsky et al. | |
| 2005/0159643 A1 | 7/2005 | Zinaty et al. | |
| 2005/0159789 A1 | 7/2005 | Brockway et al. | |
| 2005/0171398 A1 | 8/2005 | Khait et al. | |
| 2005/0177026 A1 | 8/2005 | Hoeg et al. | |
| 2005/0185299 A1 | 8/2005 | Kislev et al. | |
| 2005/0187433 A1 | 8/2005 | Horn et al. | |
| 2005/0203417 A1 | 9/2005 | Okuno | |
| 2005/0222490 A1 | 10/2005 | Glukhovsky et al. | |
| 2005/0228259 A1 | 10/2005 | Glukhovsky et al. | |
| 2005/0228275 A1 | 10/2005 | Kawashima | |
| 2005/0237631 A1* | 10/2005 | Shioya et al. | 359/770 |
| 2005/0266074 A1 | 12/2005 | Zilberstein et al. | |
| 2005/0272974 A1 | 12/2005 | Iddan | |
| 2005/0279799 A1 | 12/2005 | Kubokawa et al. | |
| 2005/0281446 A1 | 12/2005 | Glukhovsky et al. | |
| 2006/0004256 A1 | 1/2006 | Gilad et al. | |
| 2006/0009818 A1 | 1/2006 | Von Arx et al. | |
| 2006/0036131 A1 | 2/2006 | Glukhovsky et al. | |
| 2006/0045118 A1 | 3/2006 | Hyoung et al. | |
| 2006/0058663 A1 | 3/2006 | Willis et al. | |
| 2006/0074275 A1 | 4/2006 | Davidson et al. | |
| 2006/0082648 A1 | 4/2006 | Iddan et al. | |
| 2006/0092908 A1 | 5/2006 | Sung et al. | |
| 2006/0116584 A1 | 6/2006 | Sudol et al. | |
| 2006/0122461 A1 | 6/2006 | Kislev et al. | |
| 2006/0132599 A1 | 6/2006 | Iddan et al. | |
| 2006/0147037 A1 | 7/2006 | Boschetti | |
| 2006/0149132 A1 | 7/2006 | Iddan | |
| 2006/0155174 A1 | 7/2006 | Glukhovsky et al. | |
| 2006/0158512 A1 | 7/2006 | Iddan et al. | |
| 2006/0184039 A1 | 8/2006 | Avni et al. | |
| 2006/0192889 A1 | 8/2006 | Iddan et al. | |
| 2006/0206005 A1 | 9/2006 | Ou-Yang et al. | |
| 2006/0232668 A1 | 10/2006 | Horn et al. | |
| 2006/0238879 A1 | 10/2006 | Togino | |
| 2006/0252371 A1 | 11/2006 | Yanagida | |
| 2006/0252986 A1 | 11/2006 | Akagi et al. | |
| 2006/0253004 A1 | 11/2006 | Frisch et al. | |
| 2007/0002135 A1 | 1/2007 | Glukhovsky | |
| 2007/0002604 A1 | 1/2007 | Lin et al. | |
| 2007/0043310 A1 | 2/2007 | Trandafir et al. | |
| 2007/0060798 A1 | 3/2007 | Krupnik et al. | |
| 2007/0060979 A1 | 3/2007 | Strother et al. | |
| 2007/0076930 A1 | 4/2007 | Zinaty et al. | |
| 2007/0078300 A1 | 4/2007 | Zinaty et al. | |
| 2007/0078335 A1 | 4/2007 | Horn | |
| 2007/0123772 A1 | 5/2007 | Euliano et al. | |
| 2007/0185381 A1 | 8/2007 | Kimoto et al. | |
| 2007/0213659 A1 | 9/2007 | Trovato et al. | |
| 2007/0221233 A1 | 9/2007 | Kawano et al. | |
| 2007/0232874 A1 | 10/2007 | Ince | |
| 2007/0255098 A1* | 11/2007 | Wang et al. | 600/109 |
| 2007/0264732 A1 | 11/2007 | Chen | |
| 2007/0265496 A1 | 11/2007 | Kawano et al. | |
| 2007/0282156 A1 | 12/2007 | Konings | |
| 2007/0297693 A1* | 12/2007 | Lee | 382/284 |
| 2008/0015411 A1 | 1/2008 | Kimoto et al. | |
| 2008/0058597 A1 | 3/2008 | Arneson et al. | |
| 2008/0112885 A1 | 5/2008 | Okunev et al. | |
| 2008/0144701 A1 | 6/2008 | Gold | |
| 2008/0146871 A1 | 6/2008 | Arneson et al. | |
| 2008/0161660 A1 | 7/2008 | Arneson et al. | |
| 2008/0213355 A1 | 9/2008 | Bohmer | |
| 2008/0240489 A1* | 10/2008 | Marugame | 382/100 |
| 2009/0088618 A1 | 4/2009 | Arneson et al. | |
| 2009/0253999 A1 | 10/2009 | Aoki et al. | |
| 2010/0016662 A1* | 1/2010 | Salsman et al. | 600/109 |
| 2010/0130822 A1 | 5/2010 | Katayama et al. | |
| 2010/0179381 A1 | 7/2010 | Kawano et al. | |
| 2010/0194851 A1* | 8/2010 | Pasupaleti et al. | 348/36 |
| 2010/0217079 A1 | 8/2010 | Tichy | |
| 2010/0251823 A1 | 10/2010 | Adachi et al. | |
| 2010/0268058 A1 | 10/2010 | Chen | |
| 2011/0004059 A1 | 1/2011 | Arneson et al. | |
| 2011/0060189 A1 | 3/2011 | Belson | |
| 2012/0157831 A1* | 6/2012 | Waki | 600/427 |
| 2013/0308856 A1* | 11/2013 | Carpenter et al. | 382/164 |
| 2013/0329132 A1* | 12/2013 | Tico et al. | 348/571 |
| 2014/0036323 A1* | 2/2014 | Kaempflein et al. | 358/482 |
| 2014/0200418 A1 | 7/2014 | Bandy et al. | |

FOREIGN PATENT DOCUMENTS

| | | |
|---|---|---|
| EP | 1 637 917 A1 | 3/2006 |
| EP | 1 654 983 A1 | 5/2006 |
| EP | 1676522 | 7/2006 |
| EP | 1 693 000 A2 | 8/2006 |
| EP | 1 698 278 A1 | 9/2006 |
| EP | 1 704 812 A1 | 9/2006 |
| EP | 1 707 105 A1 | 10/2006 |
| EP | 1 715 697 A2 | 10/2006 |
| EP | 1 737 124 A2 | 12/2006 |
| GB | 2 414 408 A | 11/2005 |
| WO | WO 02/054932 A2 | 7/2002 |
| WO | WO 02/055126 A2 | 7/2002 |
| WO | WO 02/055984 A2 | 7/2002 |
| WO | WO 02/073507 A2 | 9/2002 |
| WO | WO 02/080376 A2 | 10/2002 |
| WO | WO 02/080753 A2 | 10/2002 |
| WO | WO 02/089913 A2 | 11/2002 |
| WO | WO 02/094337 A2 | 11/2002 |
| WO | WO 03/003706 A2 | 1/2003 |
| WO | WO 2003/001966 A2 | 1/2003 |
| WO | WO 03/010967 A1 | 2/2003 |
| WO | WO 03/028224 A2 | 4/2003 |
| WO | WO 03/053241 A2 | 7/2003 |
| WO | WO 03/069913 A1 | 8/2003 |
| WO | WO 2004/014227 A1 | 2/2004 |
| WO | WO 2004/052209 A1 | 6/2004 |
| WO | WO 2004/054430 A2 | 7/2004 |
| WO | WO 2004/058041 A2 | 7/2004 |
| WO | WO 2004/096008 A2 | 11/2004 |
| WO | WO 2005/031650 A1 | 4/2005 |

(56) References Cited

FOREIGN PATENT DOCUMENTS

| | | |
|---|---|---|
| WO | WO 2005/062715 A2 | 7/2005 |
| WO | WO 2006/005075 A2 | 1/2006 |
| WO | WO 2006/034125 A2 | 3/2006 |
| WO | WO 2006/059331 A2 | 6/2006 |
| WO | WO 2006/070367 A2 | 7/2006 |
| WO | WO 2006/103665 A2 | 10/2006 |
| WO | WO 2006/114649 A1 | 11/2006 |
| WO | WO 2007/028035 A3 | 3/2007 |
| WO | WO 2007/126246 A2 | 11/2007 |
| WO | WO 2007/126247 A1 | 11/2007 |
| WO | WO 2007/143200 A2 | 12/2007 |
| WO | WO 2007/149559 A2 | 12/2007 |
| WO | WO 2008/014432 A2 | 1/2008 |
| WO | WO 2008/016194 A2 | 2/2008 |
| WO | WO 2009/022343 A2 | 2/2009 |

OTHER PUBLICATIONS

European Patent Office. PCT Written Opinion of the International Searching Authority. International Application No. PCT/US2009/0040000. International Filing Date: Sep. 7, 2009 Applicant: Innurvation, Inc. Form PCT/ISA/237. Mailing Date: Mar. 29, 2010. 8 pages.

European Patent Office. PCT International Search Report. International Application No. PCT/US2009/0040000. International Filing Date: Sep. 7, 2009 Applicant: Innurvation, Inc. Form PCT/ISA/2210. Mailing Date: Mar. 29, 2010. 6 pages.

Kleider, et al., Preamble and embedded synchronization for Rf Carrier Frequency-Hopped OFCM, IEEE Journal on Selected Areas in Communications, vol. 23, No. 5, May 2005.

International Search Report mailed May 14, 2008 for Appln. No. PCT/US07/19379; 5 pages.

* cited by examiner

DISPLAYING IMAGE DATA FROM A SCANNER CAPSULE

CROSS-REFERENCE TO RELATED APPLICATIONS

This application is a continuation of U.S. patent application Ser. No. 12/500,232, filed Jul. 9, 2009, which claims the benefit of U.S. Provisional Application No. 61/079,342, filed Jul. 9, 2008, each of which is incorporated by reference herein in its entirety.

BACKGROUND OF THE INVENTION

1. Field of the Invention

The present invention relates generally to medical diagnostics using an ingestible medical diagnostic device, i.e. pill endoscopy.

2. Background Art

Endoscopes are commonly used by physicians to obtain images of internal tissues and organs as a diagnostic tool. Typically an endoscope is used to probe from a patient's mouth down into the upper gastro intestinal (GI) tract. During a colonoscopy, endoscopes are used to probe from the anus up into the lower GI tract. An endoscope is essentially a tube with a light and camera at its tip. Images can be transmitted outside the patient's body either optically (fiber optic cable), or converted by a camera to a digital signal and sent by wire up the endoscope and into an electronic device outside the patient.

Images presented to the physician are seen from the point of view described, i.e. looking down a tube. As a result of a complex folding of the GI tract and in combination with a fairly short distance for image capture due to low levels of lighting and/or low resolutions at far distances, only a short section of the GI tract can be viewed at any given time during an invasive procedure based on the location of the endoscope.

The population of the United States is aging. The first wave of the 78 million "Baby Boomers" is beginning to turn 60 years old. Coinciding with this aging of population is a rising concern regarding the public health, and a generally more educated patient in technology awareness. There has been an explosion in diabetes cases, estimated at 194 million cases worldwide today, and predicted to be 350 million cases by year 2025. Obesity currently affects two thirds of the U.S. population. There is a rising incidence of cardiac problems for women (the #1 cause of death for women). Hepatitis C will soon reach epidemic levels, infecting nearly 5 million people, more than the number of approximately 1.2 million people infected with HIV/AIDS in the U.S. Celiac disease affects approximately 3 million people in the U.S., with about 97% being undiagnosed. The prevalence of further serious conditions, such as cancer, ultra- or ulcerative-colitis, lactose intolerance, allergies, etc., indicate that there is a need for simple and easy diagnostic techniques, especially because many of these diseases are chronic, requiring repeat testing over time. Some conditions, such as cancer, are most responsive to treatment if caught in the early stages. Cancer, for example, is best detected in the digestive tract. Given that cancerous growth can occur in as little as one to two years, it is essential to detect cancer or cancerous precursors at least annually, or preferably biannually. Physician and health care resources are currently already stretched and will fail if the current technology, process and procedure are not altered to suit the needs of the baby boomer market of the near future. Time-saving and simple solutions to testing are needed.

The current population desires speedy testing and fast answers to their health questions. Many current testing and monitoring systems are limited by old technology and processes that take days, if not weeks, for results. These test methods, if not inconvenient and potentially embarrassing, are at least in most cases intrinsically painful or risky to patients.

One ingestible diagnostic device in the market today is a disposable RF camera pill or capsule camera, which captures images of the digestive tract as it passes through. Current camera pill usage by patients and physicians is limited for several reasons. First and foremost, current technology is very large in comparison to most ingestible medicines and nutritional supplements. The excessive size is in part a result of the selection of power-inefficient communication methods. The large size mandates pre-screening of patients (an additional process, inconvenience, and cost). The large size also leads to a reasonably high potential that the device can become lodged within the GI tract. This may lead to a highly invasive surgical removal requirement, which carries all the risks associated with some surgeries.

Conventional RF camera pills require a bulky reading device worn as a belt around the waist and adhesive sensors attached to the body to capture an electromagnetically-coupled signal transmitted from the pill. The patient is required to report to a physician's office for prescreening, to initiate use of the camera pill, and to be fitted with the belt reader. The belt reader is worn for 24 hours, during which time the camera pill captures images and transmits the images to the reader belt. At the end of a diagnosis period, the patient (and belt reader) must return to the physician. The physician downloads images from the belt reader and analyzes the images. The physician may analyze the images and discuss the results with the patient at yet another appointment during a subsequent visit. Thus, current RF camera pills require at least two trips to the physician's office, as well as the wearing of a cumbersome belt reader with leads attached to the skin.

This diagnostic process is both inconvenient and uncomfortable. It also carries a risk of surgical removal, due to the size of the current camera pills. Current technology does not offer a recorded position within the body associated to the specific image taken. Physicians must achieve a location of an image of interest through yet another procedure. Furthermore, the current camera pills are expensive devices, and are resorted to when other bowel disease diagnostic techniques, such as endoscopy and colonoscopy (each of which are extremely intrusive), present results that need farther investigation. Further, the electromagnetic signals used to transmit the images may harm the sensitive tissue they pass through in order to be detected outside the body. Therefore, the current ingestible camera pill has significant deficiencies.

Current technology RF camera pills attempt to mimic the imaging carried out by physicians using laparoscopes and endoscopes. The camera pill illuminates the GI tract as it passes through and takes pictures at regular intervals, much like frames of a movie. The physician later views a series of images in a format of a movie that when paused appear much like images provided by an endoscope. Due to the natural movement of the digestive tract, the resultant movies from the current camera pills depict spurts of forward and backward movements that are awkward and not reviewer friendly, leading to issues of reviewer focus and overall system effectiveness.

What is needed is a way to display a high resolution image captured by a new generation of ingestible image scanning pills to a medical professional in a manner that allows the professional to easily find, zoom in on and get context for any abnormalities that may be observed.

BRIEF SUMMARY OF THE INVENTION

This section is for the purpose of summarizing some aspects of the present invention and to briefly introduce some preferred embodiments. Simplifications or omissions may be made to avoid obscuring the purpose of the section. Such simplifications or omissions are not intended to limit the scope of the present invention. Consistent with the principles of the present invention as embodied and broadly described herein, the present invention includes an ingestible image scanning pill which is able to capture high resolution images of the wall of the GI tract as it passes through it propelled by peristaltic action. The peristaltic action produces a forward and backward, churning motion as an aid to the digestive process. Images of the GI tract are captured by "scanning" line by line and region by region the GI tract as the pill moves through it. Images are obtained not by "photographing" as in many of the known technologies, but rather by "scanning" line by line and area by area. The GI tract can be illuminated by various types of sources including white light, multi-spectrum light, narrow spectrum light, infra-red, ultra-violet, and even non-light energies such as, for example, acoustical energy, etc.

Images communicated outside of the patient represent tissues at exact locations determined based on signals transmitted. Such images can be communicated by radio wave, optically (such as, for example, using an optical fiber), by acoustic signals, etc. Signals representing images are received outside the patient's body and are processed by one or more computers running software capable of discarding duplicate information and stitching together, line scan by line scan a complete GI tract as if it were stretched out in a straight line. The processed, fully linear image is then displayed to a medical professional as if the GI tract had been stretched into a straight line, cut open, laid flat out on a bench for viewing— all without making any incisions in a live patient, as easy as swallowing a pill.

The image processing software is capable of concurrently rendering different aspects on the GI tract, similar to topology views created by computer software of terrain as would be viewed from the top or 'flown through' from the side to side. Aspects from a dissection viewpoint (laid out on a table), to a close-up dissection view, to a generated looking down the tube viewpoint.

Alternative form factors to a "pill" can also be used, such as, for example, a modified endoscope or modified catheter.

Further features and advantages of the invention, as well as the structure and operation of various embodiments of the present invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

Figure 4:
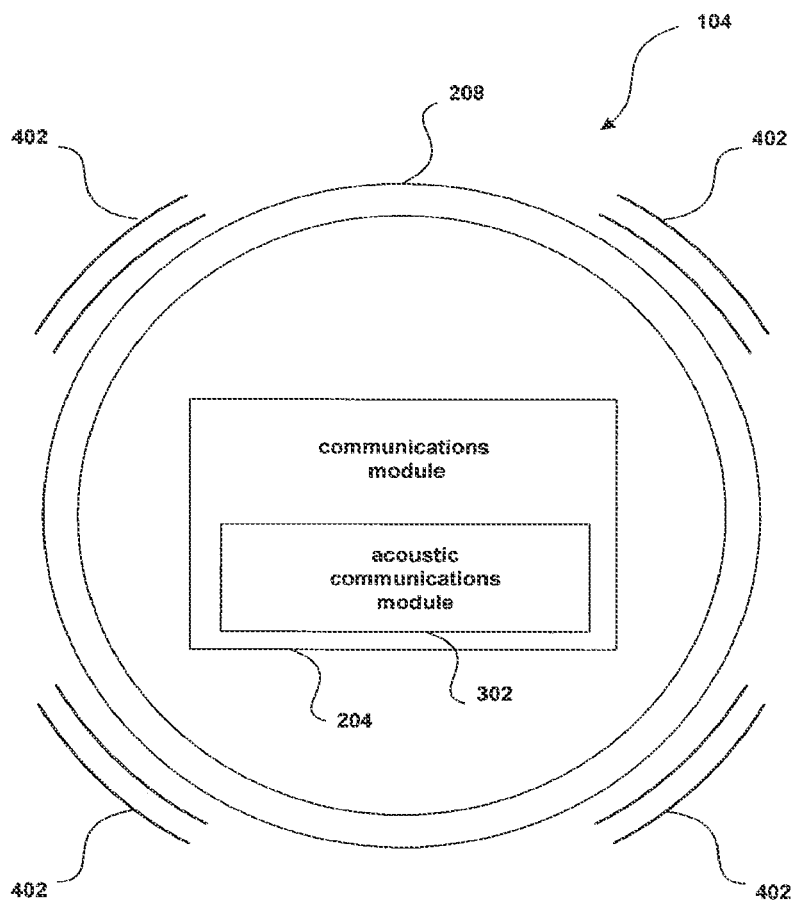

FIG. 4 shows a view of ingestible capsule 104, with communications module 204 including acoustic communications module 302.

Figure 5:
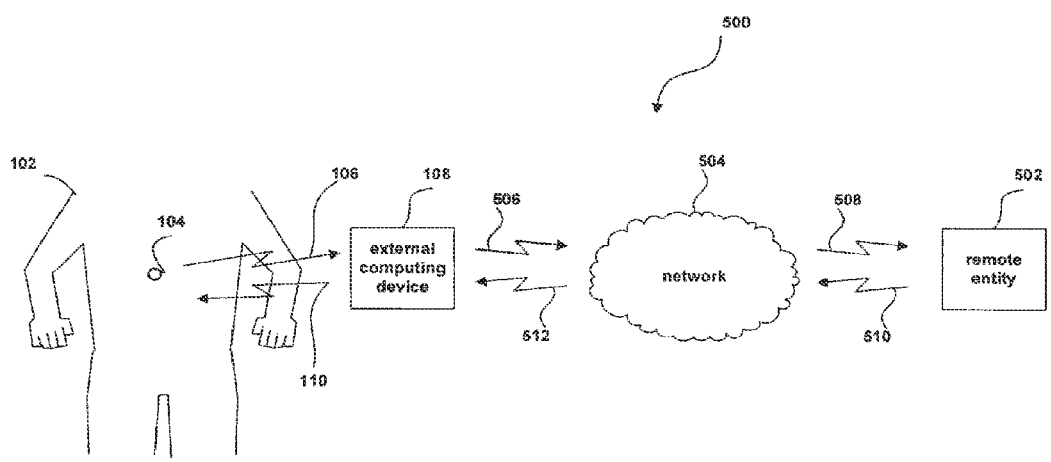

FIG. 5 is a schematic diagram of an example sensor communications network.

Figure 6:
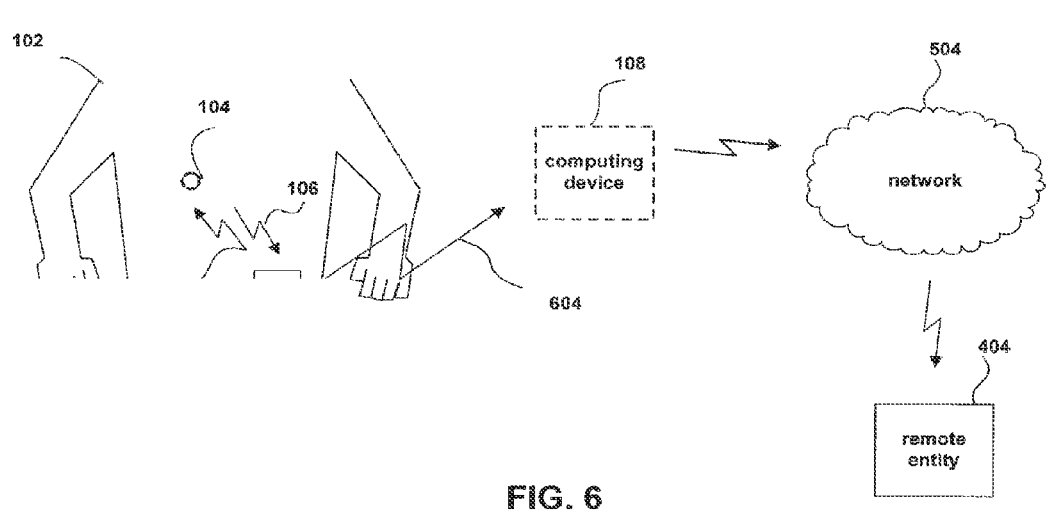

FIG. 6 is a schematic illustrating how ingestible capsule 104 may also communicate with computing device 108 via an intermediate sensor link module 602.

Figure 7:
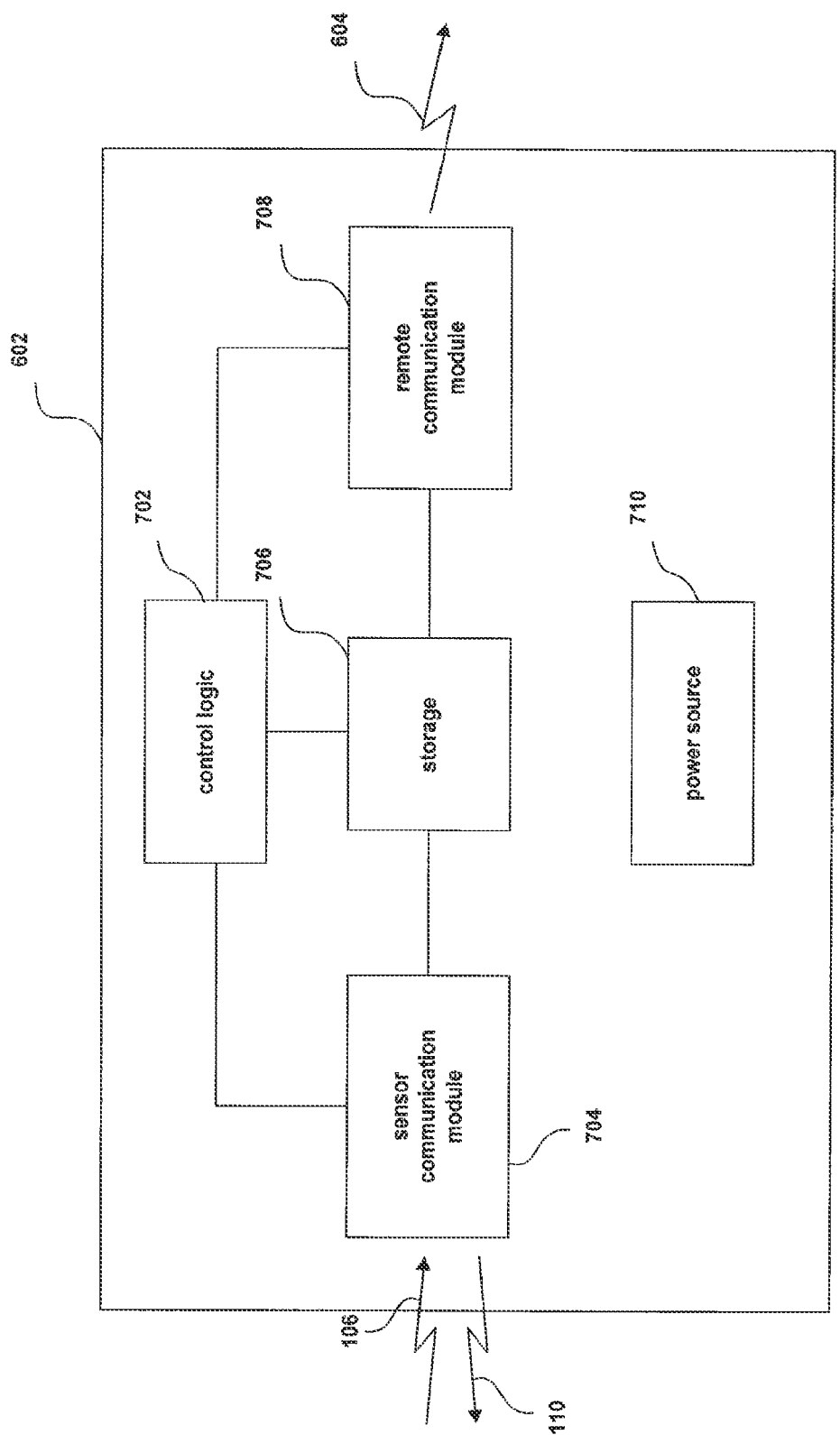

FIG. 7 is a schematic diagram illustrating how a sensor link module 602 may be configured in various ways.

Figure 8:
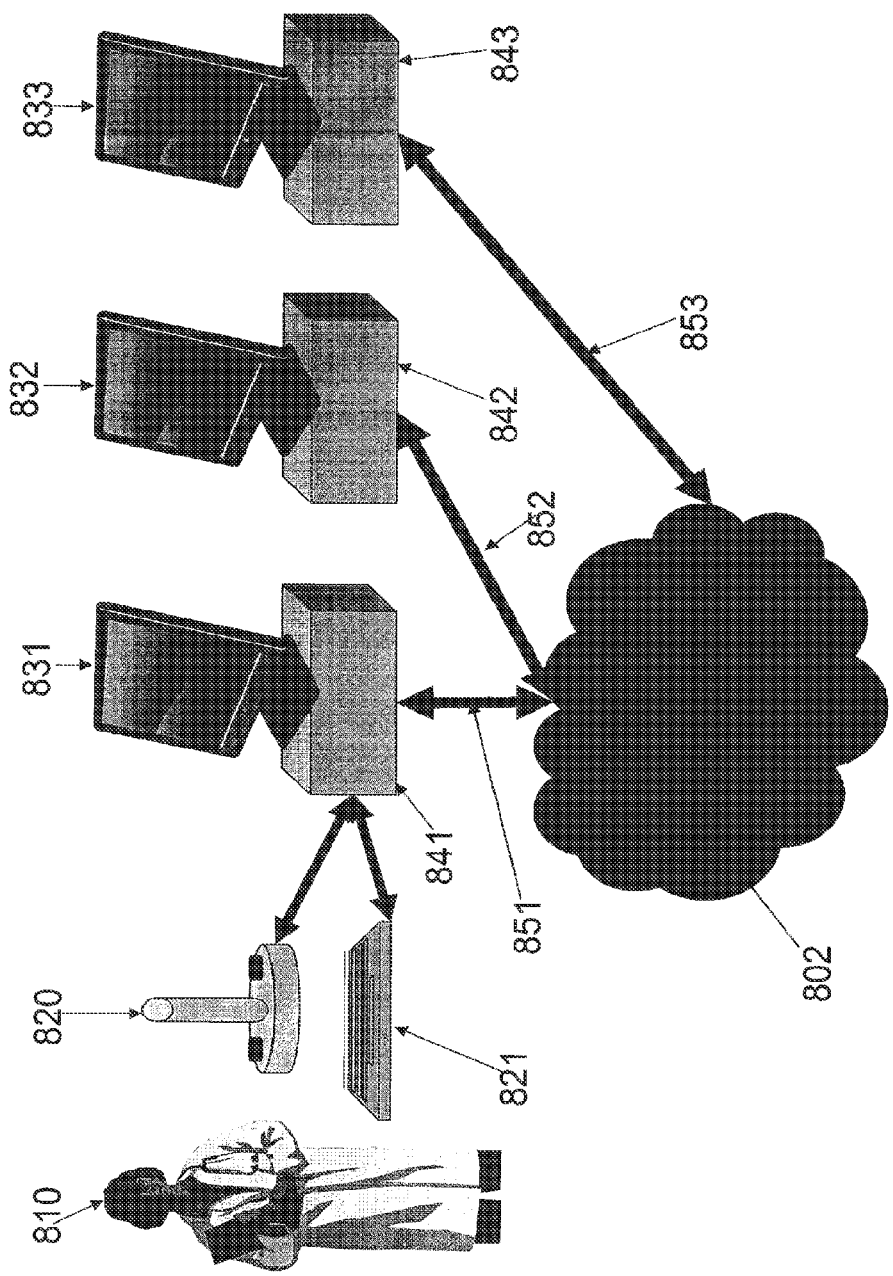

FIG. 8 depicts a system for display utilizing multiple computer processors each connected directly to a monitor for display.

Figure 9:
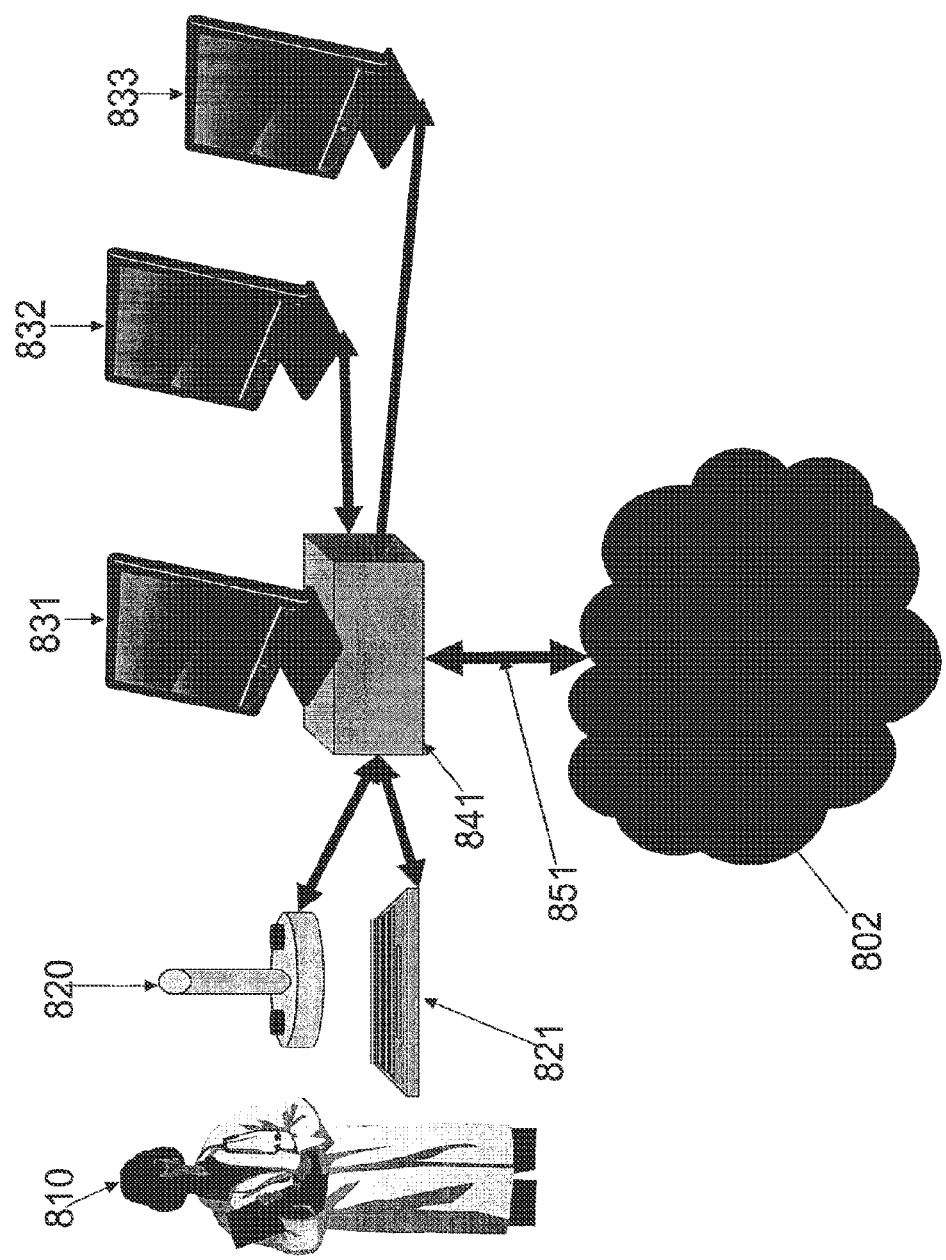

FIG. 9 depicts a system for display utilizing multiple monitors connected to a single processor for display.

Figure 10:
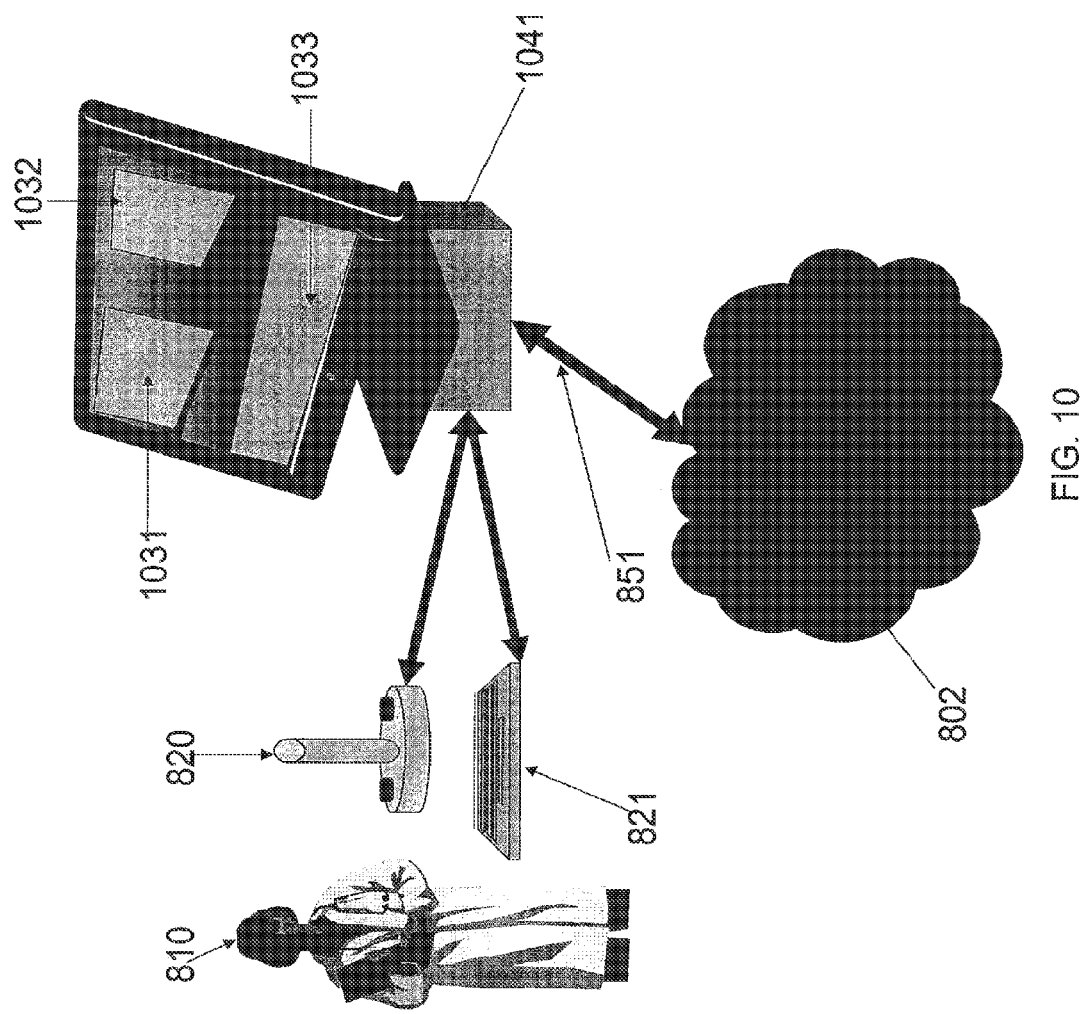

FIG. 10 depicts a single display and single processor with multiple windows each with a display of information.

Figure 11:
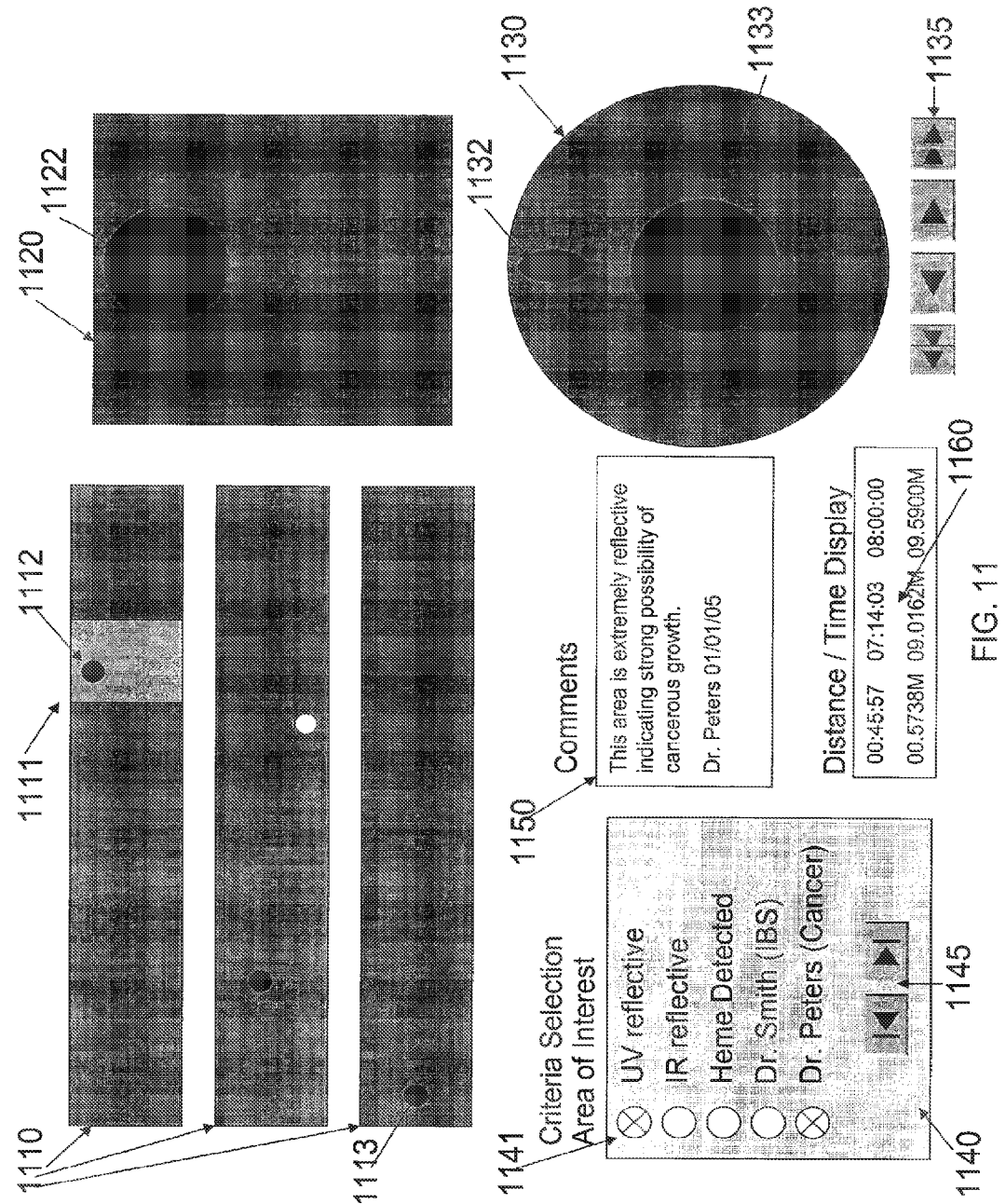

FIG. 11 depicts information for display for an image scanner capsule

Figure 12:
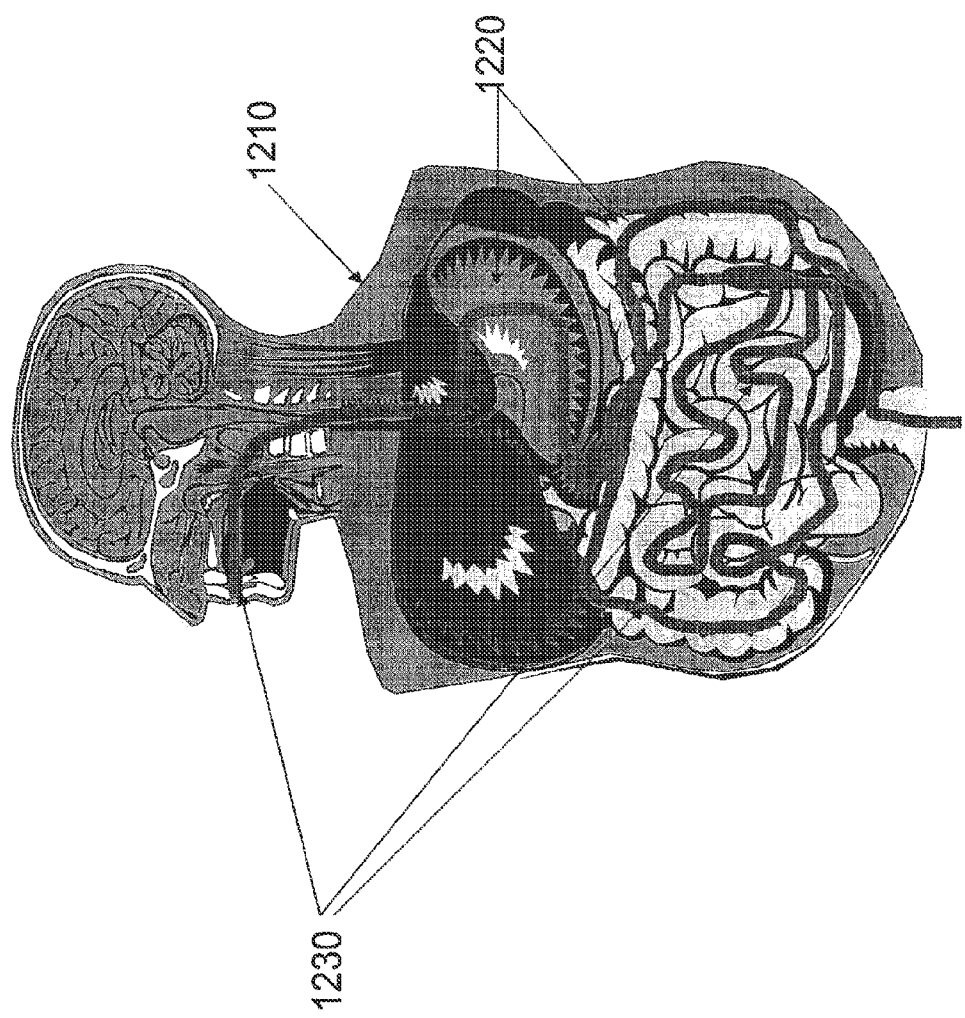

FIG. 12 depicts a normalized human subject and mapping of GI tract within.

Figure 13:
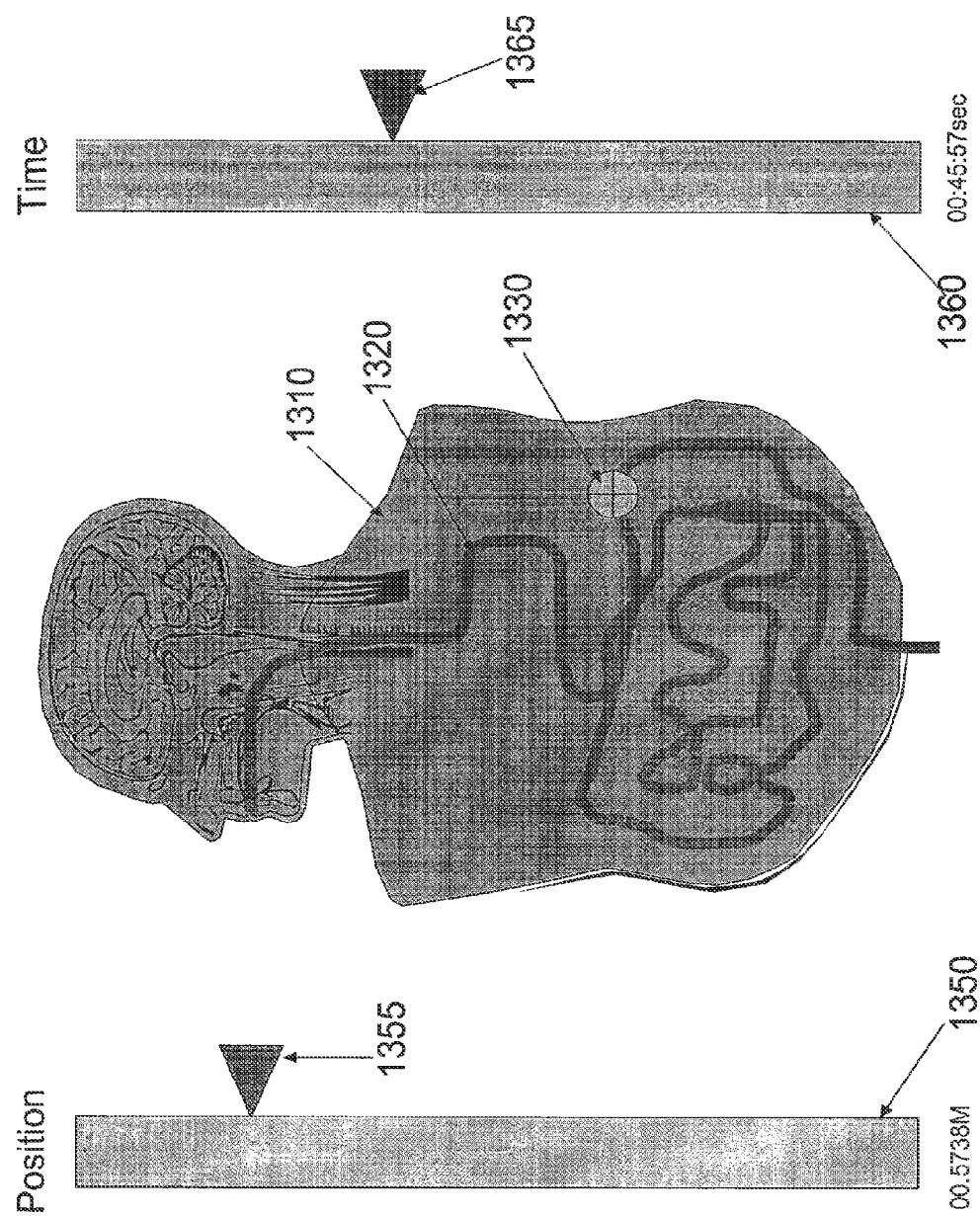

FIG. 13 depicts a display of an ingestible capsule path as it transits a GI tract with several positional controls.

Figure 14:
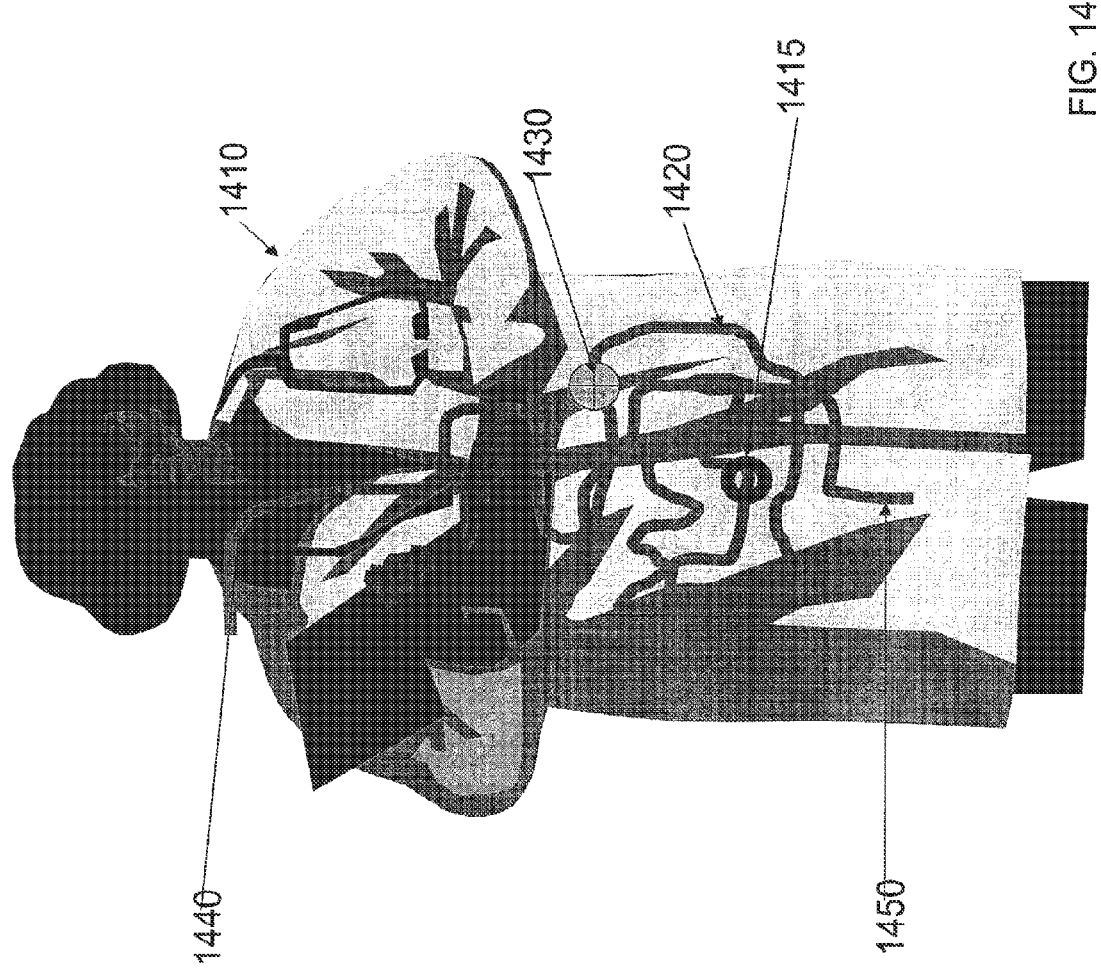

FIG. 14 depicts a projection of an ingestible capsule path and icons for areas of concern upon a patient's body.

Figure 15:
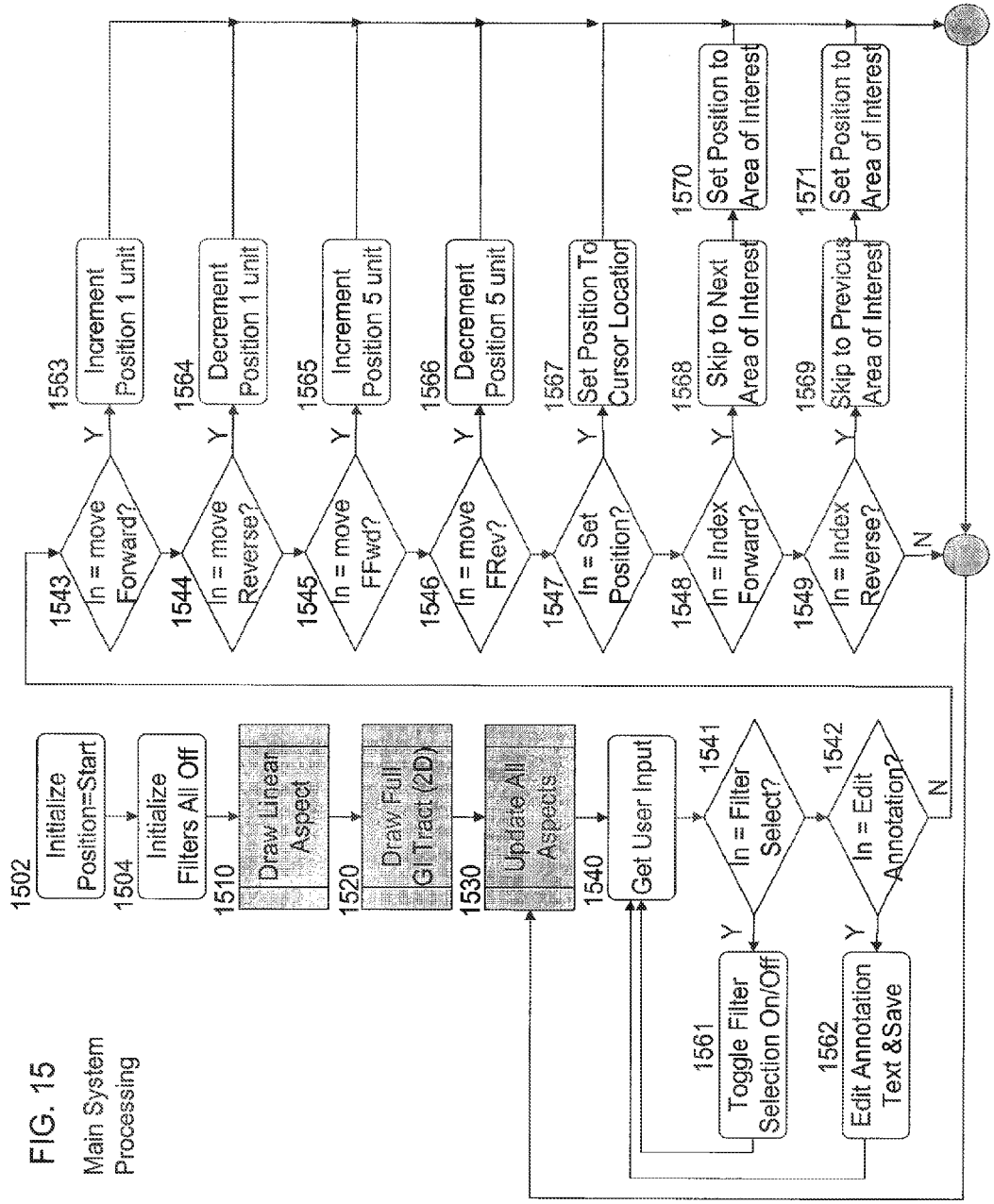

FIG. 15 is a flow chart of a main processing system of image processing software for rendering the displays depicted in FIG. 11.

Figure 16:
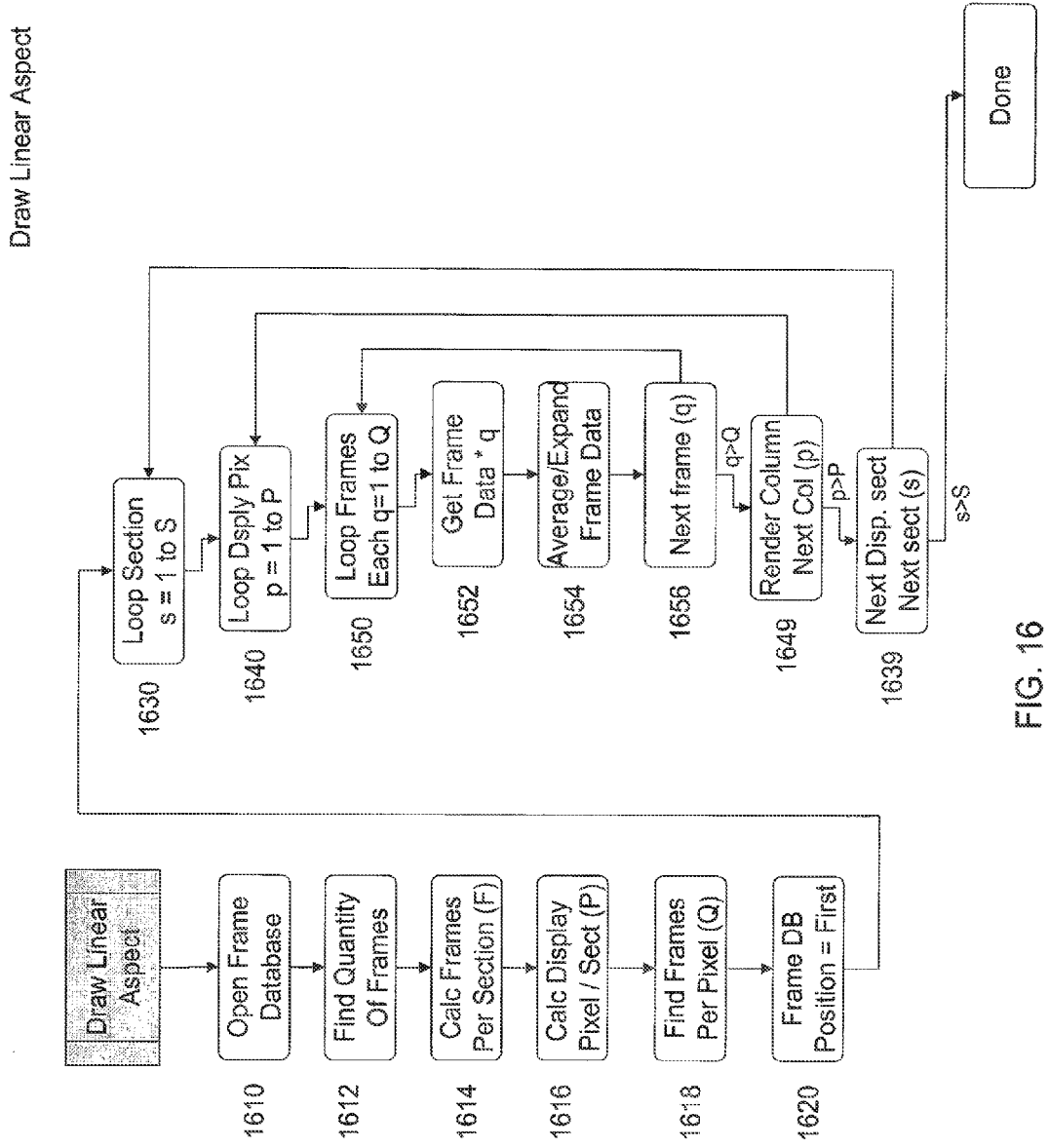

FIG. 16 is a flow chart of a subroutine of the image processing software for rendering a linear aspect of the displays depicted in FIG. 11.

Figure 17:
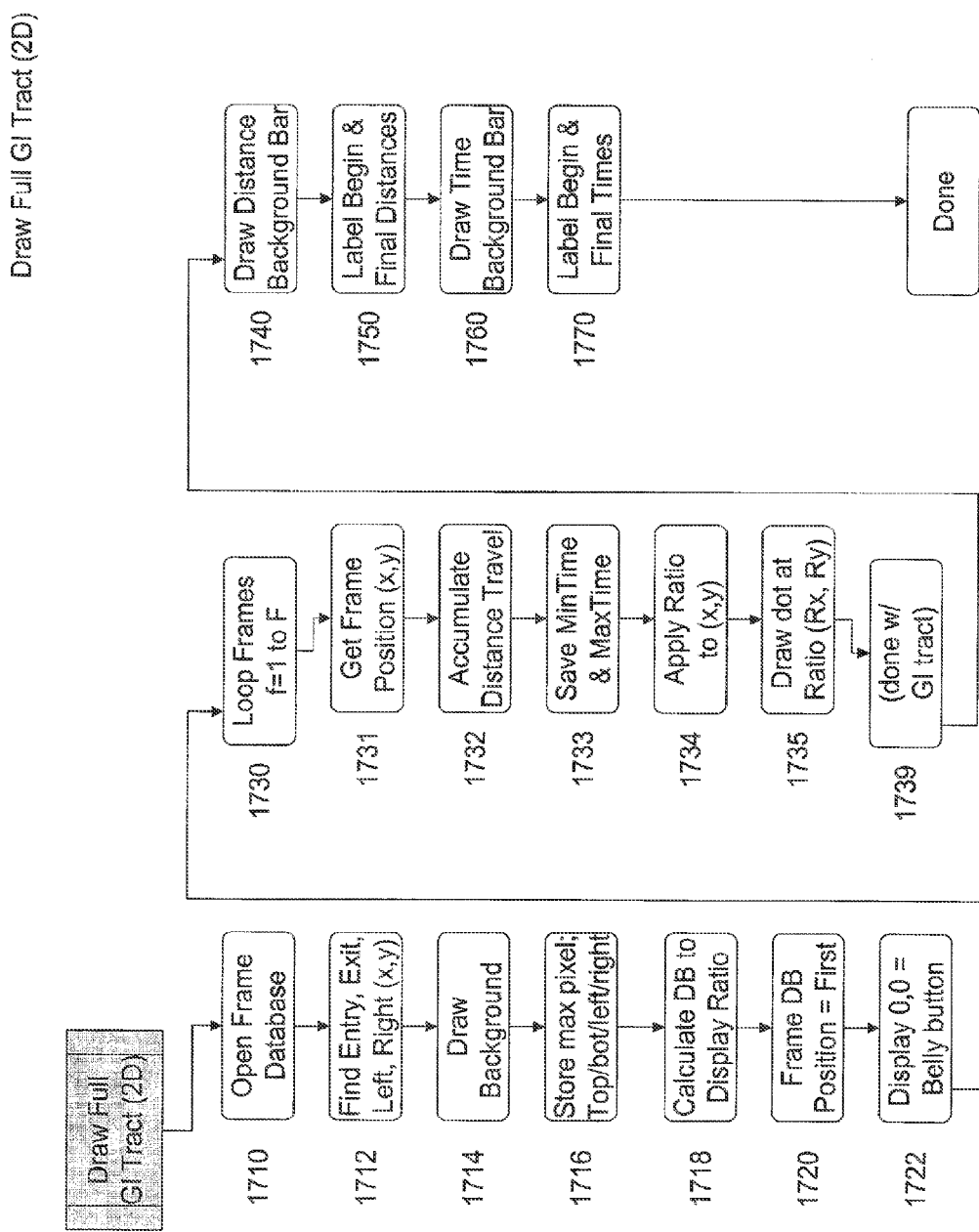

FIG. 17 is a flow chart of a subroutine of image processing software for rendering a drawing of the full GI tract in 2D.

Figure 18:
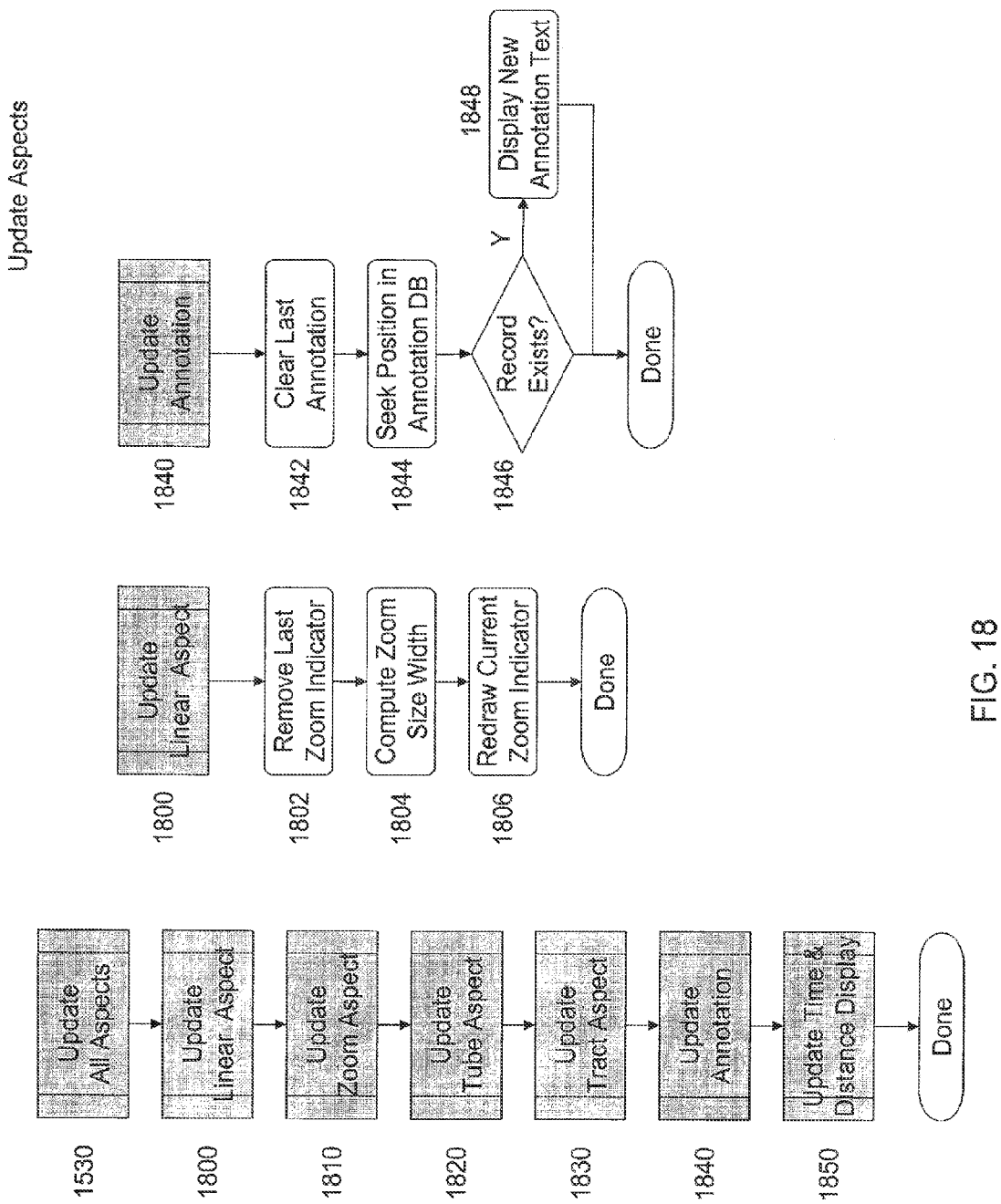

FIG. 18 is a flow chart of subroutines of image processing software for updating aspects of the displays and providing annotations as depicted in FIG. 11.

Figure 19:
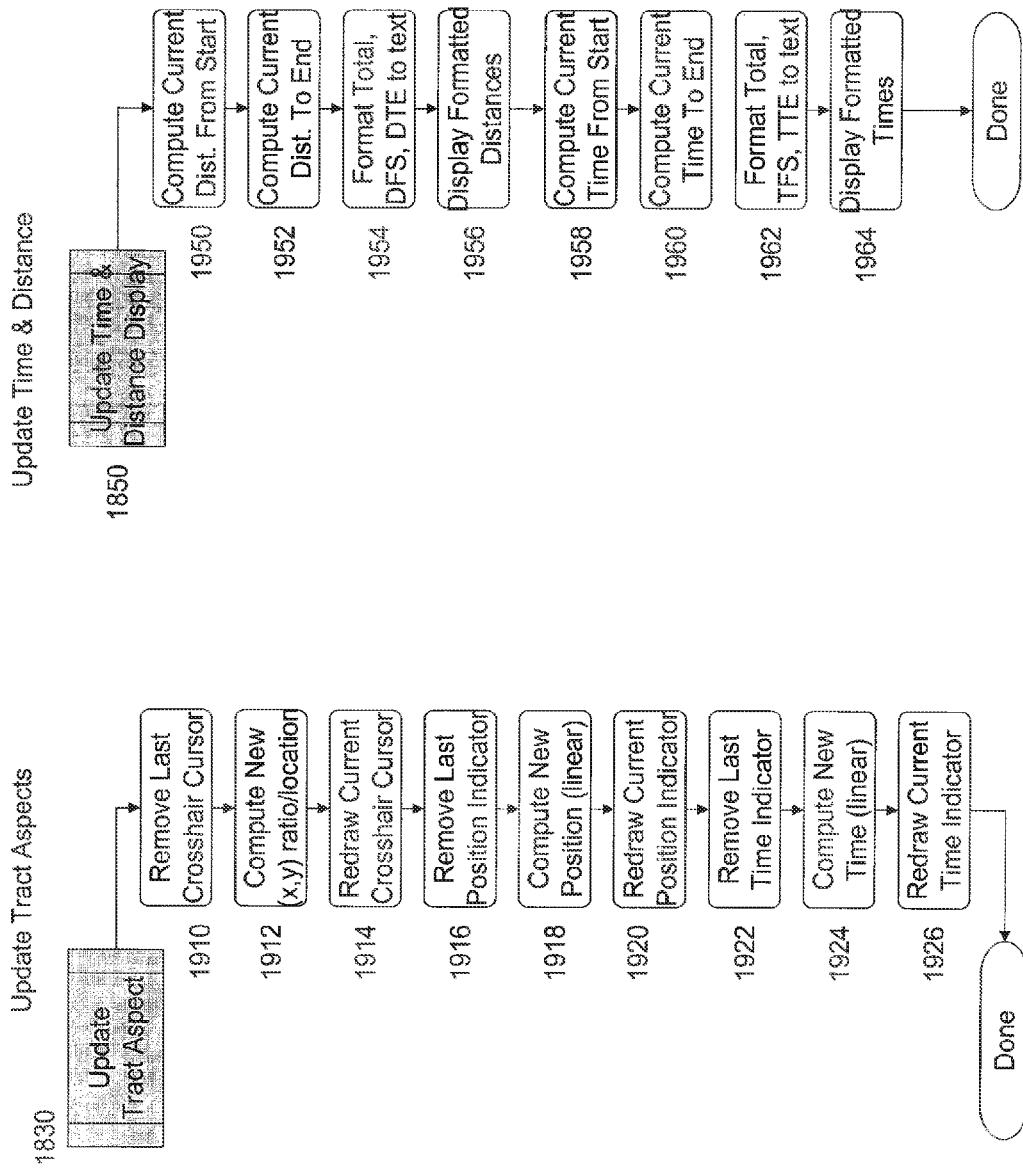

FIG. 19 includes flow charts of subroutines of the image processing software for updating a tract aspect and updating time and distance, respectively, of the displays depicted in FIG. 11.

Figure 20:
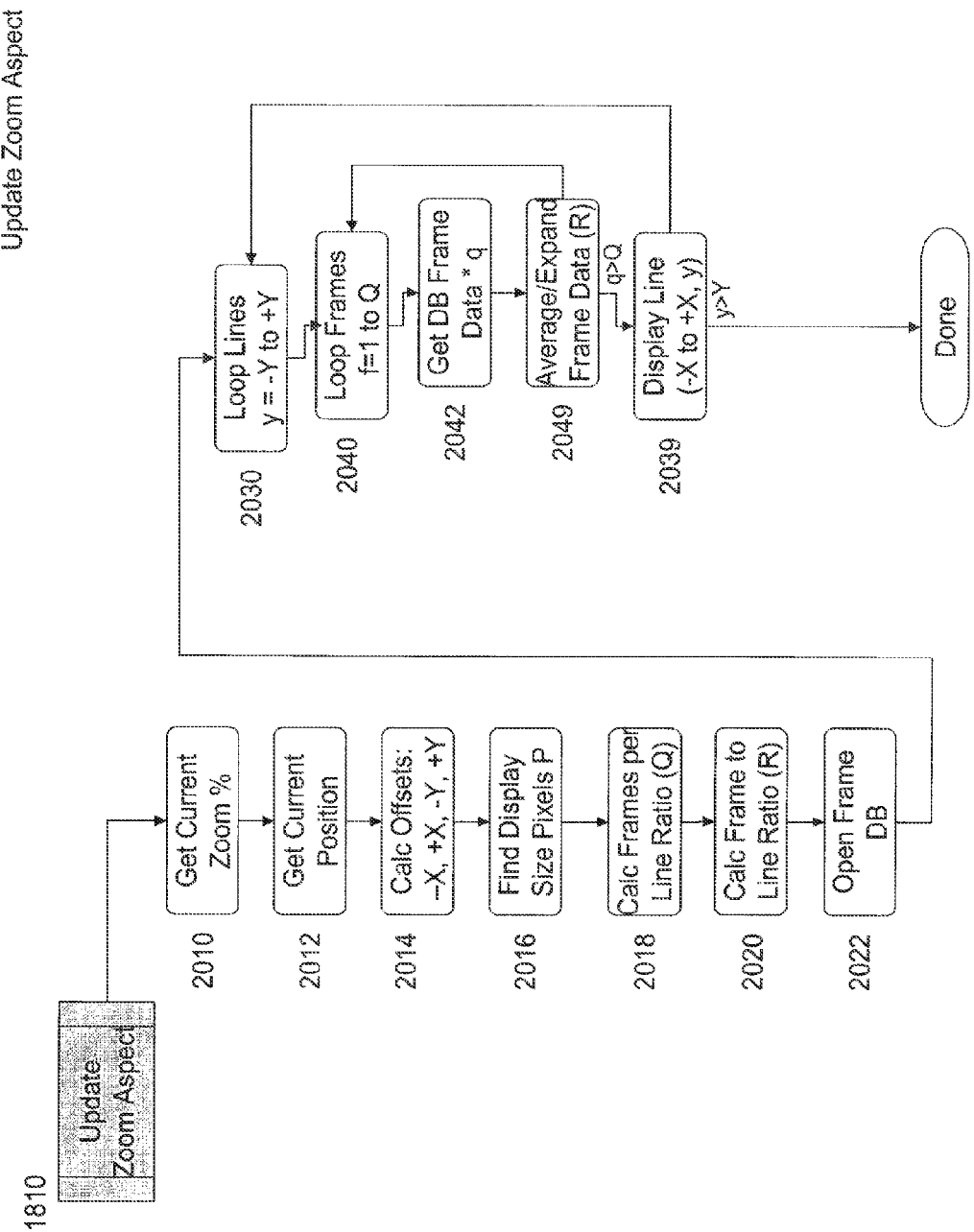

FIG. 20 is a flow chart of a subroutine of image processing software for updating a zoom aspect.

Figure 21:
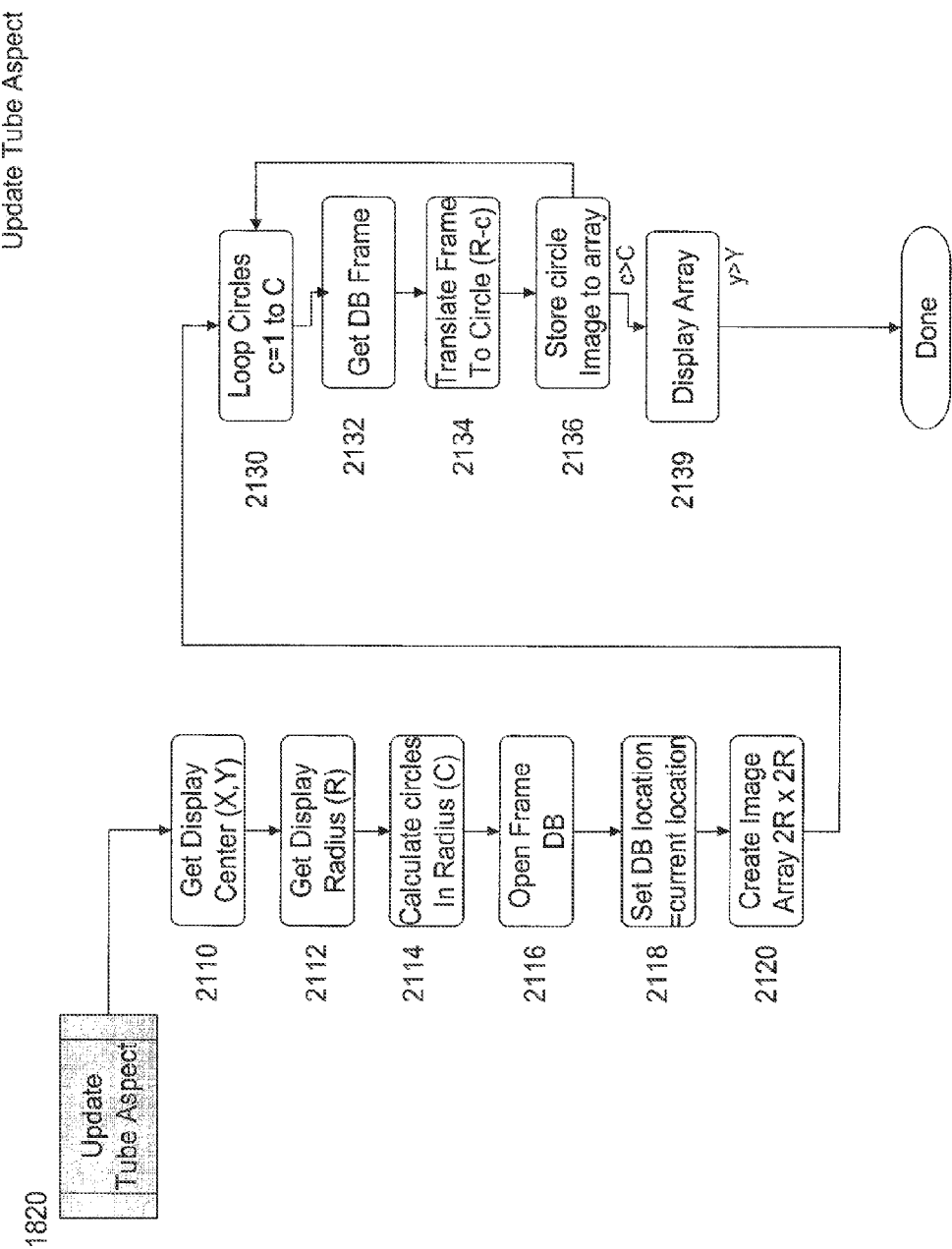

FIG. 21 is a flow chart of subroutines of image processing software for updating a tube aspect.

Figure 22:
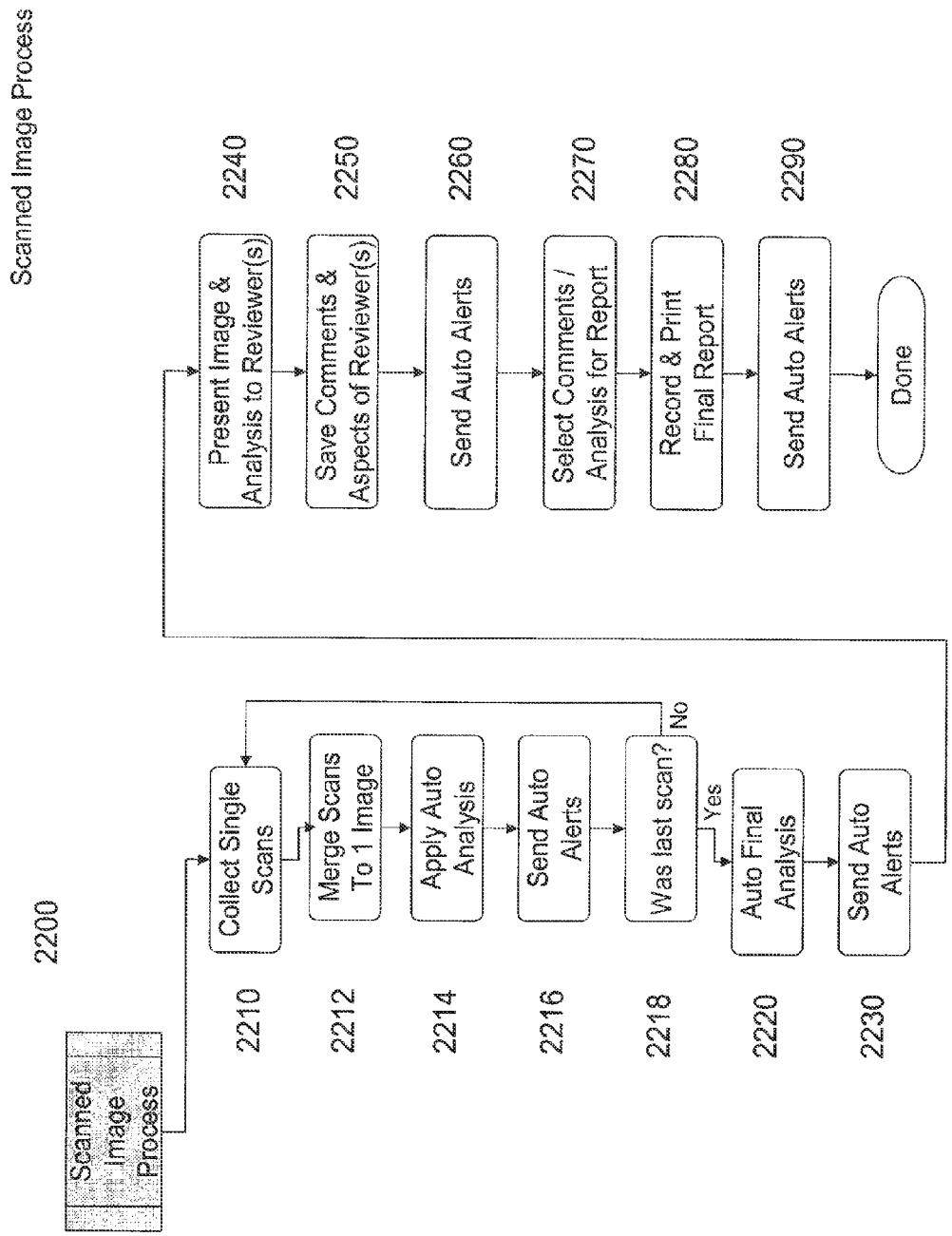

FIG. 22 is a flow chart of an overall scanned image collection, processing, and reporting system.

Figure 23:
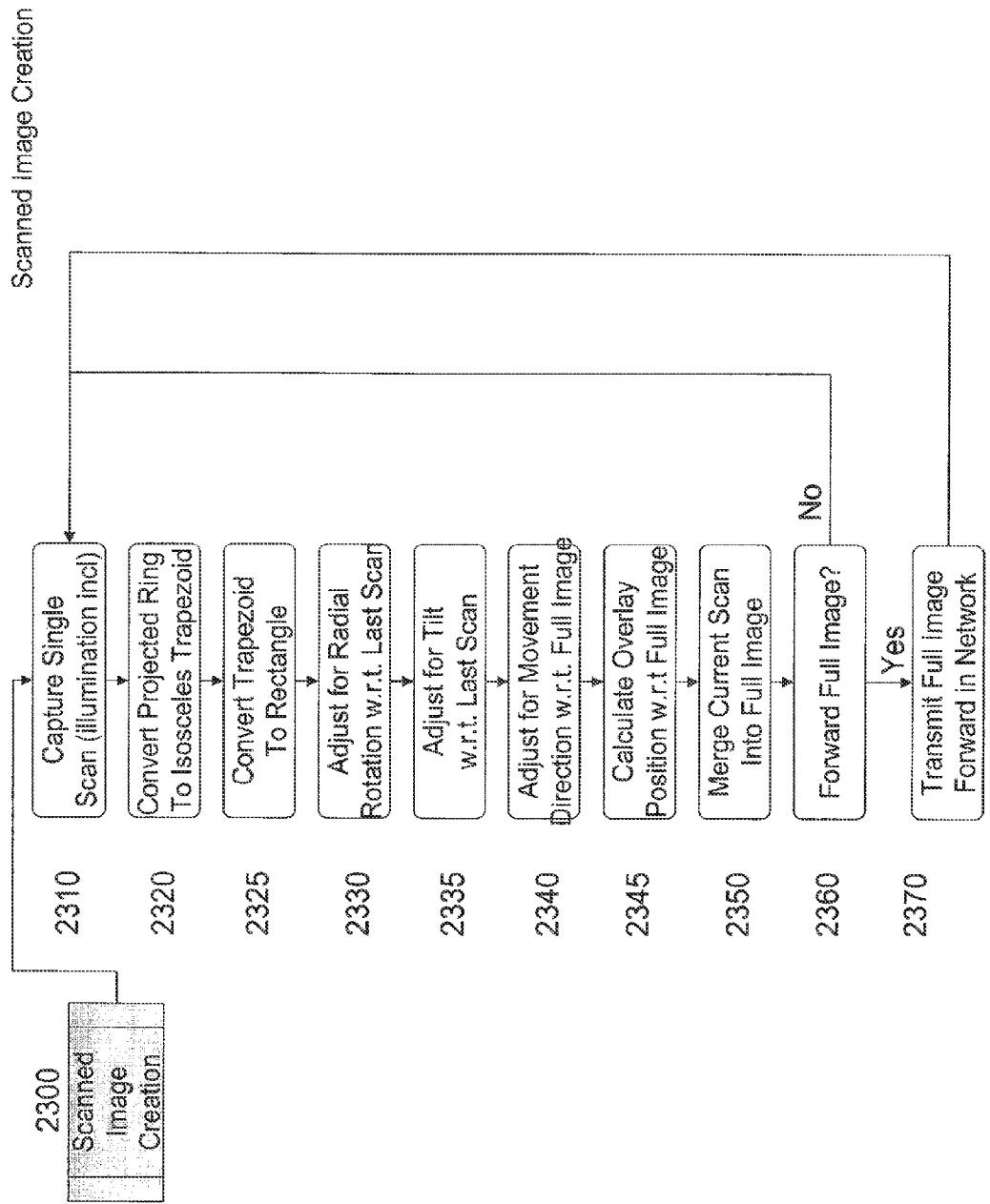

FIG. 23 is a detailed flow chart of a scanned image creation process.

Figure 24:
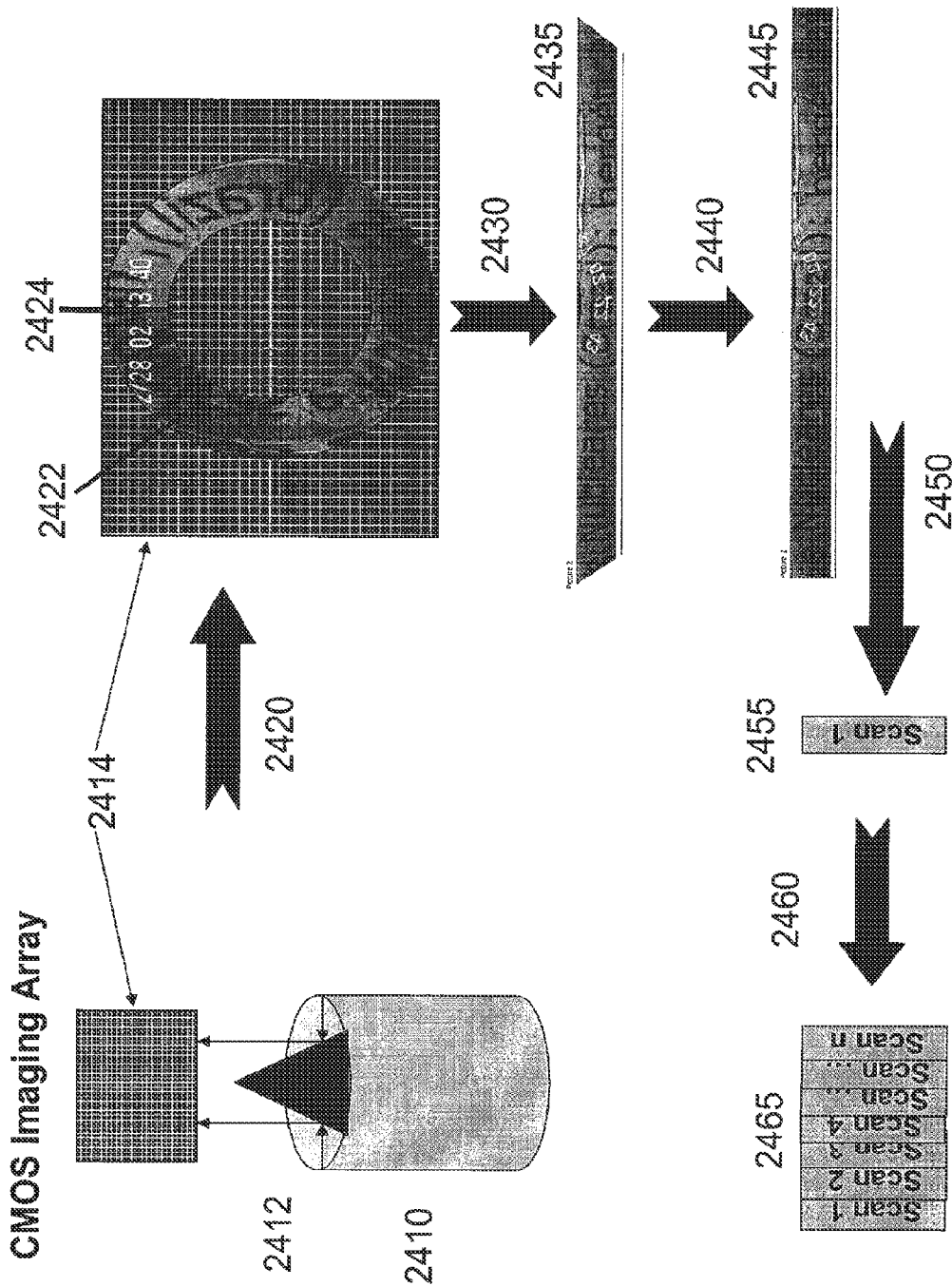

FIG. 24 is an exemplary depiction of scanned data corresponding to FIG. 23 process.

Features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION OF THE INVENTION

Introduction

The invention will be better understood from the following descriptions of various "embodiments" of the invention. Thus, specific "embodiments" are views of the invention, but each does not itself represent the whole invention. In many cases individual elements from one particular embodiment may be substituted for different elements in another embodiment carrying out a similar or corresponding function. It is to be appreciated that the Detailed Description section, and not the Summary and Abstract sections, is intended to be used to interpret the claims. The Summary and Abstract sections can set forth one or more but not all exemplary embodiments of the present invention as contemplated by the inventor(s), and thus, are not intended to limit the present invention and the appended claims in any way.

The arrangements and techniques described herein are particularly suitable for improved imaging using an ingestible diagnostic pill, although they are applicable to other devices, such as for example, laparoscopes and endoscopes.

An ingestible image scanning pill captures high resolution images of the GI tract as it passes through. Examples of such scanning pills are described in U.S. patent application Ser. No. 11/851,221, filed Sep. 6, 2007, titled "Ingestible Low Power Sensor Device and System for Communicating with Same," and U.S. Provisional Patent Application No. 61/028,102, filed Feb. 12, 2008, titled, "Ingestible Endoscopic Optical Scanning Device," each of which is incorporated by reference herein in its entirety. Images communicated externally have exact location determination. Example techniques for locating a diagnostic pill are set forth in U.S. patent application Ser. No. 11/851,179, filed Sep. 6, 2007, titled "Imaging and Locating Systems and Methods for a Swallowable Sensor Device, which is incorporated by reference herein in its entirety. Image processing software discards duplicate information and stitches images together, line scan by line scan a complete GI tract as if it were stretched out in a straight line. Stitching can be completed during the scanning process (real time) or alternatively can be batch processed after all scan information is collected, or completed through a periodic batch process (pseudo-real time). After a full image or a pseudo-real time partial image is available, automated image analysis functions will each insert their results into a database with an index into the available image and offset within the image. A fully linear image with optional automated analysis results is displayed to a medical professional as if the GI tract had been stretched in a straight line, cut open, laid flat out on a bench for viewing and optionally with suspect abnormalities indicated—all without making any incisions in a live patient. The medical professional will review the image and suspected areas of abnormality and also insert their own suspected areas and/or general comments into a database similar to that of the automated analyses. Finally, the medical professional will optionally create a report of findings with, among other details and comments, a selection of suspected abnormalities and their corresponding images at the same aspect of their review. A system may be automated so as to automatically generate alerts when stages are complete, such as when a full image is available, when a report of findings is complete, or when automated image analysis is completed.

The invention is described in terms of specific embodiments that each incorporate certain features of the invention. The embodiments merely exemplify the invention. It is not intended that each embodiment include all features of the invention. The scope of the invention is not limited to the disclosed embodiments. The invention is defined by the claims appended hereto.

References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Furthermore, it should be understood that spatial descriptions (e.g., "above," "below," "up," "left," "right," "down," "top," "bottom," "vertical," "horizontal," etc.) used herein are for purposes of illustration only, and that practical implementations of the structures described herein can be spatially arranged in any orientation or manner. Likewise, particular bit values of "0" or "1" (and representative voltage values) are used in illustrative examples provided herein to represent data for purposes of illustration only. Data described herein can be represented by either bit value (or by alternative voltage values), and embodiments described herein can be configured to operate on either bit value (or any representative voltage value), as would be understood by persons skilled in the relevant art(s).

The example embodiments described herein are provided for illustrative purposes, and are not limiting. Further structural and operational embodiments, including modifications/alterations, will become apparent to persons skilled in the relevant art(s) from the teachings herein.

Ingestible Diagnostic Pill

The embodiments described herein are set forth in the context of an ingestible diagnostic pill. The following provides general explanation about the configuration and arrangements of ingestible diagnostic pills suitable tor making use of the inventions described herein.

The example embodiments of an ingestible diagnostic pill described herein are provided for illustrative purposes, and are not limiting. Further structural and operational embodiments, including modifications/alterations, will become apparent to persons skilled in the relevant art(s) from the teachings herein.

Structures and methods for an ingestible diagnostic pill are described. An ingestible diagnostic pill is also referred to as an "ingestible capsule" because of its generally capsule shape. It is also referred to an "ingestible pill" or "diagnostic pill." The ingestible diagnostic pill may be swallowed by a human (or animal) to diagnose or aid in the diagnosis of one or more conditions through either an immediate detection or a historical and/or statistical analysis of multiple detections of conditions or attributes over a time period. Example embodiments are described below as related to a human subject, for illustrative purposes. However, embodiments of the present invention are applicable to animals other than humans, including livestock (cattle, sheep, pigs, chickens, turkeys, ostriches, etc.), pets (e.g., dogs, cats, horses, etc.), and other animals of interest such as race horses or other performance/sport animals. Such applicability to these types of animals, and other types, will be apparent to persons skilled in the relevant art(s) from the teachings herein, and is within the scope and spirit of embodiments of the present invention.

Furthermore, example embodiments are described below as related to passing an ingestible capsule through a gastrointestinal tract, for illustrative purposes. However, embodiments of the present invention are applicable to further bodily systems other than the gastrointestinal tract, including the circulatory system, the urinary tract, and other bodily systems and additionally other means of entry or implant into a body cavity of an animal or human. Such applicability to other types of bodily systems will be apparent to persons skilled in the relevant art(s) from the teachings herein, and is within the scope and spirit of embodiments of the invention.

Figure 1:
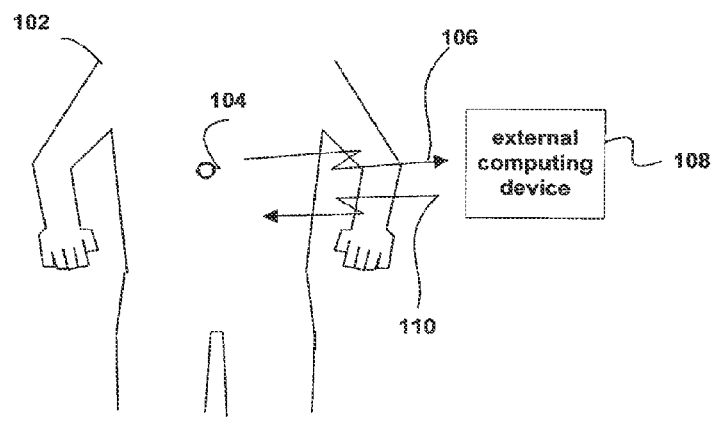
FIG. 1 shows a partial view of a human 102 according to an embodiment of the present invention.

FIG. 1 shows a partial view of a human 102 according to an embodiment of the present invention. In FIG. 1, human 102 has swallowed or ingested an ingestible capsule 104. Ingestible capsule 104 is configured to sense one or more attributes or conditions of human 102 as ingestible capsule 104 passes through human 102. While passing through human 102, ingestible capsule 104 transmits information in a communication signal 106 to, be received on the outside of the human 102. Ingestible capsule 104 may send information to and receive information from an external device, via communication signal 110, or it may be a beacon that only emits information to the external device. As shown in FIG. 1, an external computing device 108 may receive communication signal 106. Computing device 108 may be used to display the information received in communication signal 106, to interact with the information, to process the information, and/or to transmit the information (raw or processed) to another entity or component. In an embodiment, computing device 108 can interact with ingestible capsule 104 to control functions of ingestible capsule 104.

In embodiments, human 102 may be provided with one or more ingestible capsules 104 that human 102 may at designated times and/or periodically swallow to perform an analysis of one or more health-related conditions of human 102. Multiple ingestible capsules 104 may interact with device 108 and/or each other.

Figure 2:
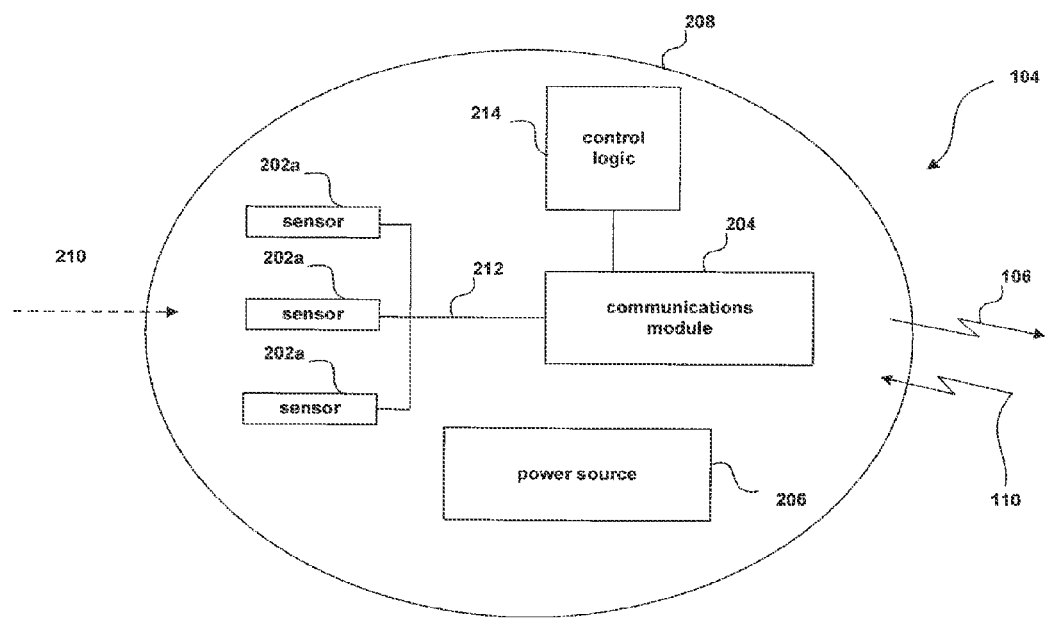
FIG. 2 shows an example block diagram of ingestible capsule 104, according to an embodiment of the present invention.

FIG. 2 shows an example block diagram of ingestible capsule 104, according to an embodiment of the present invention. In FIG. 2, ingestible capsule 104 includes an acoustically transmissive encapsulation 208 that holds one or more sensors 202, a communications module 204, and a power source 206. Although FIG. 2 illustrates ingestible capsule 104 as having three sensors 202a, 202b, and 202c, one of skill in the art will recognize that any number of sensors may be included in ingestible capsule 104. In one embodiment, there may be no sensor(s) 202 at all, providing a capability to track the pill movement in space, hence allowing a mapping of a gastro-intestinal tract and also the time of movement within that tract.

In an embodiment were ingestible capsule 104 has one or more sensor(s) 202, sensor(s) 202 are used to sense (e.g., measure, detect, etc.) a received stimulus 210, and generate a sensor output signal 212. Sensor output signal 212 may be a digital or analog signal, depending on the particular implementation of sensor 202. In alternative embodiments the acoustically transmissive encapsulation 208 may be made of sensor(s) 202, or sensor 202 may be integrated within the materials known as acoustically transmissive encapsulation 208. Ingestible capsule 104 can include any number of sensors 202, each of which may all sense the same condition or may sense a different condition than another sensor 202. Sensor 202 may detect and/or interact directly with conditions of the body. Sensor 202 may also detect and/or interact with signals emanating from the pill and reflecting off nearby tissues, such as is the case with, for example and without limitation, a camera or optical scanner detecting light that originates from the capsule, ultrasonic detectors, and radioactivity sensors. In an embodiment, sensor 202 detects reflections of signal 106 from nearby gastro-intestinal and other body tissues.

Logic control 214 initiates activity of sensor 202 via control connection 211. Sensor 202 detects or interacts with the body and produces a sensor output signal 212. Communications module 204 receives sensor output signal 212, and generates communication signal 106 to include information based on sensor output signal 212. Communication signal 106 is transmitted from ingestible capsule 104.

Figure 3:
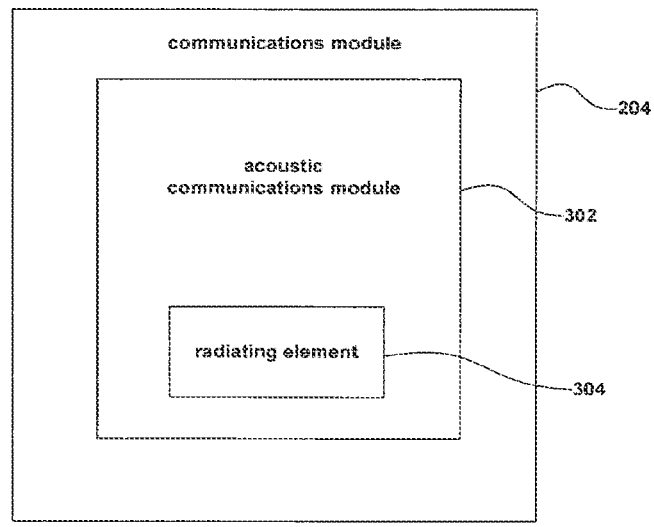
FIG. 3 is a schematic diagram of a communications module according to an embodiment of the invention.

In an example embodiment, as shown in FIG. 3, communications module 204 may include an acoustic communications module 302, configured to transmit and/or receive an acoustic communications signal. For example, acoustic communications module 302 may include an acoustic transmitter. Sensor output signal 212 is modulated on an acoustic signal that is transmitted as communications signal 106 by the acoustic transmitter. The acoustic communications signal 106 may be transmitted by radiating element 304, which may be, for example, an electromechanical transducer or piezoelectric (e.g., PZT, PVDF, etc.) element or transducer that vibrates at acoustic frequencies. An example acoustic frequency range in which acoustic communication signal 106 may be transmitted is 20 Hz to 3 MHz, although the frequency may be an acoustic frequency higher or lower than this range in some applications. An example frequency for acoustic communications signal 106 is 2 MHz. In a likewise fashion, acoustic communications module 302 may include an ultrasonic communications module, configured to transmit and/or receive a communications signal at ultrasonic frequencies (e.g., greater than 20 KHz). Communications module 204 may be configured to modulate information of sensor output signal 212 according to a variety of modulation techniques, including amplitude modulation (AM), frequency modulation (FM), and phase modulation (PM), and including any combination of these modulation techniques, including in quadrature modulation schemes. Acoustic pressures according to embodiments may have various levels, including greater or lower than 1 Pa, including in the KPa (or greater) range to the μPa (or less) range.

FIG. 4 shows a view of ingestible capsule 104, with communications module 204 including acoustic communications module 302. In FIG. 4, communications module 204 is coupled to acoustically transmissive encapsulation 208. Acoustically transmissive encapsulation 208 vibrates according to acoustic communications module 302 to transmit a communications signal 402, which is an acoustic version of communications signal 106. In FIG. 4, acoustically transmissive encapsulation 208 functions as an acoustic radiating element, vibrating at acoustic frequencies according to acoustic communications module 302.

Returning to FIG. 2, operation of ingestible capsule 104 may be gated and controlled by control logic 214, which itself may be operating in a sub-threshold voltage (Vt) manner (e.g., to save power), or control logic 214 may operate in normal bias modes. In an embodiment, ingestible capsule 104 is an autonomous device with one way communication (transmission capability), so that control logic 214 may be extremely simple, and thus would not consume much power even when operating in normal bias modes. However, in another embodiment, ingestible capsule 104 may communicate in both directions, and may be configured to receive instructions from computing device 108. Control logic 214 may thus have additional complexity in order to, for example, decode and implement received instructions.

Power source 206 provides power (e.g., via electrical energy) to operate the components of ingestible capsule 104 that require power, such as communications module 204 and/or sensor 202. Power source 206 may include, for example and without limitation, a battery, a liquid, or an energy harvesting module.

In an embodiment, ingestible capsule 104 is configured for low power operation, including extreme low power (XLP) operation. To achieve XLP operation, ingestible capsule 104 can use one or both of a very small battery and energy harvesting to operate ingestible capsule 104. In an embodiment, circuits of ingestible capsule 104 are implemented in one or more integrated circuits (ICs), in a technology such as CMOS, or other technology. The IC(s) and any other internal components of ingestible capsule 104 may be mounted to a circuit board, or mounted directly to acoustically transmissive encapsulation 208. Thus, in embodiments, power source 206 is configured for low power output, including supplying power in the milliwatt and microwatt ranges. Such low power requirements enable the size of power source 206 to be minimal.

In a CMOS embodiment, MOSFET circuits may be configured to operate in a deep sub-threshold voltage (sub-Vt) mode, which lowers their switching time to acoustic switching frequencies, and lowers their power consumption, by orders of magnitude. In such a mode the MOSFET devices operate as analog devices. Such operation was demonstrated in the mid-1980's by Carver Meade with regard to eye and ear chips. Such a mode of operation eliminates the need for digitizing the sensor information, which can be very power intensive, and which further reduces the power consumption by a large factor.

Acoustically transmissive encapsulation 208 contains sensor 202, communications module 204, and power source 206, and is configured to be ingestible by or inserted within a human and/or animal. Acoustically transmissive encapsulation 208 may be the size of a vitamin or other type of pill that is ingestible by humans. For example, acoustically transmissive encapsulation 208 may be approximately 3 mm in diameter and approximately 5 mm in length. Acoustically transmissive encapsulation 208 may be any suitable shape, including oval, elliptical (as shown in FIG. 2), capsule shaped, or spherical. The small size of acoustically transmissive encapsulation 208 allows ingestible capsule 104 to be easily ingested by an average human 102. Further, the small size of acoustically transmissive encapsulation 208 increases the ability of ingestible capsule 104 to pass completely through the digestive system of a human 102 without becoming trapped due to size incompatibility.

Acoustically transmissive encapsulation 208 may be made from a variety of non-digestible or slow rate of digestion materials, including: a plastic material, such as a resin, a resinoid, a polymer, a cellulose derivative, a casein material, and/or a protein; a metal, including a combination of metals/alloy; a glass material; a ceramic; a composite material; and/or other material/combination of materials. In a particular embodiment, acoustically transmissive encapsulation 208 may be comprised of a material that aids in the sensing of biological, chemical, or other attributes of body material that touches or comes in close proximity to the acoustically transmissive encapsulation 208, such as could be called an integrated encapsulation and sensor material.

After being swallowed by human 102, ingestible capsule 104 eventually passes from human 102, such as when human 102 has a bowel movement to excrete waste. In an embodiment, ingestible capsule 104 is disposable. In another embodiment, ingestible capsule 104 may be recovered, (and recycled) for reuse.

Depending upon the ability or control of the patient, ingestible capsule 104 may alternatively be inserted into a lower gastrointestinal tract of human 102 as a suppository device.

Depending on the configuration of sensor 202, while passing through human 102, ingestible capsule 104 can sense conditions and/or features of any part of the gastrointestinal tract, and any of the materials/fluids contained within and/or secreted by the organs in the gastrointestinal tract or organs indirectly associated with the gastrointestinal tract. Ingestible capsule 104 can also receive conditions or signals from even more remote body organs such as acoustic pickup of heartbeat and/or breathing and more indirect conditions such as temperature. In an embodiment, a camera or an optical scanning imaging system is coupled to ingestible capsule 104 to allow visual observation of human 102.

As mentioned, ingestible capsule 104 transmits information in communication signal 106 to be received outside human 102, such as by computing device 108. In an embodiment, computing device 108 may be configured to communicate with a remote entity 502, such as shown in an example sensor communications network 500 shown in FIG. 5. Computing device 108 may be configured to communicate with remote entity 502 using wired and/or wireless links, in a direct fashion or through a network 504. For example, computing device 108 transmits a communication signal 506 to network 504, which transmits a communication signal 508 to remote entity 502. Network 504 may be any type of network or combination of networks, such as a telephone network (e.g., a land line and/or cellular network), a personal area network (PAN), a local area network (LAN), and/or a wide area network (WAN) such as the Internet.

Remote entity 502 may be one or more of a variety of entities, including a human and/or computer-based entity. For example, remote entity 502 may include a diagnosing physician who receives information collected by ingestible capsule 104 (and optionally processed by computer device 108) in communication signal 508.

As shown in FIG. 5, sensor communications network 500 may include a return communications path from remote entity 502 through network 504 to computing device 108. For example, a return communication signal 510 is transmitted by remote entity 502 to network 504, which transmits a return communication signal 512 to computing device 108. In this manner, remote entity 502 (e.g., diagnosing physician and/or computer system) can provide feedback to computing device 108 in communication signal 512 regarding the analysis of human 102 performed by ingestible capsule 104. Return communication signal 512 may include any type of data/information format for providing the feedback, including an email, a text message, a text file, a document formatted for commercially available word processing software, a proprietary document/data format, auditory alarms, alerts and messages, etc.

Ingestible capsule 104 may also communicate with computing device 108 via an intermediate sensor link module 602, as shown in FIG. 6. Sensor link module 602 receives communication signal 106 from sensor 202. Sensor link module 602 transmits a communication signal 604 to computing device 108, to provide the information sensed by sensor 202 to computing device 108. For example, sensor link module 602 may be used when ingestible capsule 104 communicates using an acoustic communications signal having a power level too low to reliably be received by computing device 108. As shown in FIG. 6, sensor link module 602 is coupled to human 102.

In another embodiment, sensor link module 602 may provide a communication interface between ingestible capsule 104 and network 504, such that a separate computing device 108 is not required. In such an embodiment, sensor link module 602 may perform functions of computing device 108 described above, and thus sensor link module 602 may be referred to as a computing device.

Multiple sensor link modules 602 may provide a capability of location detection through triangulation and other algorithms, capable of detecting sensor device 104 to a very accurate, three (3) dimensional location within human 102. In ah embodiment, multiple sensor link modules 602 may be attached to human 102 at various locations in order to receive the interior acoustic signal from different angles. Sensor link module 602 may be, for example, directly attached to the skin of human 102, such as by an adhesive or a strap. Sensor link module 602 may be attached to human 102 in one or more locations, including the head, neck, chest, back, abdomen, arm, leg, etc. With regard to receiving communication signal 106 from ingestible capsule 104 passing through the gastrointestinal tract, ingestible capsule 104 may be attached to the neck, chest, back, and/or abdomen for a short signal path.

An amount of received information is proportional to the number of sensor link modules 602 attached to human 102. The array of sensor link modules 602 may be attached at specific locations on human 102 to increase, and even maximize, the received diagnostic information. Multiple sensor link modules 602 can identify a specific location of the ingestible capsule which can be used for linking a location to the detection of a sensed material. The location can also be used to identify a historical analysis of the track taken by the ingestible capsule and the speed of passage.

For example, the attachment of an array of three or more sensor link modules 602 to human 102 may enable triangulation or other location finding algorithms to be used to locate ingestible capsule 104 in human 102. Alternatively, one or more sensor link modules 602 having three or more receivers each may be used to the same effect. By locating ingestible capsule 104 in human 102, a location of a sensed material in human 102 can be determined.

In embodiments, sensor link module 602 may be configured in various ways. For instance, FIG. 7 shows an example sensor link module 602, according to an embodiment of the present invention. As shown in FIG. 7, sensor link module 602 includes control logic 702, a sensor communication module 704, storage 706, a remote communication module 708, and a power source 710.

Sensor communication module 704 receives communication signal 106 from ingestible capsule 104. Sensor communication module 704 demodulates the sensor-related information of communication signal 106. Furthermore, sensor communication module 704 may process and/or convert a format of the information received in communication signal 106. For example, sensor communication module 704 may perform an analog-to-digital (A/D) conversion of the received sensor information, and outputs a sensor information signal. The sensor information signal may be received by storage 706 and/or by control logic 702.

Storage 706 is configured to store the sensor information of the sensor information signal. Storage 706 may include any type of suitable storage, including a hard drive and/or memory devices. Storage 706 can output the stored information in a stored sensor information signal, for subsequent transmission to computing device 108 by remote communication module 708.

Control logic 702 is configured to control operation of sensor link module 602.

Remote communication module 708 receives the stored sensor information signal, and formats the sensor-related information for transmission. Furthermore, remote communication module 708 transmits the sensor information in communication signal 604. Remote communication module 708 may be configured to transmit communication signal 604 in a variety of formats/protocols, such as a standard RF communication protocol including Bluetooth, IEEE 802.11, Zigbee, or other communication protocol, standard or otherwise. For example, in embodiments, computing device 108 may be a Bluetooth, 802.11, and/or Zigbee configured handheld device such as cell phone, personal digital assistant (PDA), a Blackberry™, wrist watch, music player, or laptop, or other type of computer, handheld, desktop, or otherwise. Remote communication module 708 may also transmit an identification number assigned to ingestible capsule 104 for identification by a receiver.

Power source 710 provides power to elements of sensor link module 602 that require power, such as control logic 702, sensor communication module 704, storage 706, and remote communication module 708. For example, power source 710 may include one or more batteries that are rechargeable or non-rechargeable. Power source 710 may also (or alternatively) include an interface for externally supplied power, such as standard A/C power.

As described above, in an embodiment, ingestible capsule 104 can transmit an acoustic signal. By receiving the acoustic signal transmitted by ingestible capsule 104, sensor link module 602 may perform a type of ultrasound analysis based on the human interior generated acoustic signal from ingestible capsule 104. As acoustic communication signal 106 is transmitted through human 102 from ingestible capsule 104, signal 106 is transformed by attenuation, refraction, and reflection, as a function of the tissue of human 102 that signal 106 passes through. The transformed signal thus provides additional diagnostic information to sensor link module 602, very much like a diagnostic ultrasound conveys diagnostic information that can be analyzed by a trained technician. The acoustic signal from ingestible capsule 104 may be viewed as an "interior" ultrasound or "sonogram", which can be analyzed to extract additional diagnostic information regarding human 102. In an embodiment, information received by sensor link module 602 regarding the interior ultrasound signal can be used to generate a graphical display of at least a portion of the interior of human 102. An interior ultrasound can also be generated from an array of PZT sensors configured around the circumference of the capsule, which would receive the ultrasound signal reflected by the tissue of the body lumen. The captured ultrasound image data would then be sent from the capsule to sensor link module 602.

Image Process

FIG. 22 depicts an overall system flow process for the acquisition, display, and diagnosis of image data from, for example, an ingestible scanning capsule, according to an embodiment of the present invention. In the first process, 2210, image data is captured on the capsule and transmitted to storage on a network resource as described in FIGS. 5 and 6. In Step 2212, these single scans of 2210 are manipulated into a single image. As could be expected, combining these multiple individual scans into a single image is quite complex, and a topic described below. Following this process, in step 2214, is an automated image analysis step, which may trigger alerts to nurses, doctors, and other health professionals in step 2216. Automated image analysis may look for patterns, colors, transit distance, and even compare known image libraries for abnormalities. Step 2216 alerts may inform a health professional that a capsule has entered a certain area, for instance, a stomach, small bowel, or large bowel, or have completed passage of the entire digestion system. Additionally, step 2216 may send alerts as to emergency conditions such as bleeding, stoppage of the passage of the capsule, or potentially critical findings of cancerous regions or substantially large foreign objects, as well as other alerts for operations of equipment and medical diagnostic findings. Step 2218 determines if the scan is a last scan of interest—and the last image data to be compiled into a single large image of the intestinal tract. Several conditions may trigger the last scan conclusion—a capsule out of battery indication, a loss of communication (capsule out of body, for example), a distance traveled (either determined on the capsule, an adjacent receiver, or even a function on the network), an automated process concluding the end of a desired region (for example, small bowel).

Once a final inclusive scan is determined and received, a final processing can occur upon the collective image. In step 2220, optionally, automated analysis is launched upon the full image. Functions can be identical to those in step 2214, however, functions such as total length, size, coloration, and a variety of comparison to the whole will likely be accomplished after the last scan is received. The final automated analysis functions in step 2220 may include determination of the segments of the intestinal tract, such as stomach, small bowel, and large bowel, but may also include the numerous detailed parts known to medical professionals. Automated analysis functions will detail findings as well as the location and aspect (zoom, color filtering, etc) within the final full image. For instance, a detected cancer region may be more easily viewed and recognized at a zoomed out, general area image (akin to a city level on a Google map), and with no red colorization that might obscure the cancer tissue. In comparison, as another example, evaluation of Celiac's disease, which erodes the villi of the intestinal wall, might be best evaluated with a close-up image (akin to Google's street level) in full color.

After each and/or all of a potential of multiple automatic analyses, notifications of the progress would be sent in step 2230. Alerts may be directed to one or multiple recipients, such as medical professionals for evaluation of the imagery and analyses, doctor office staff for scheduling of equipment return, patient appointments, and scheduling final doctor review of the imagery & analyses, or even to the patient for equipment return or to call in for an appointment. In step 2240, medical professionals will be presented with the resultant scanned imagery, results of automated or external analyses of the imagery, and will have the opportunity to explore the imagery from different magnification levels, colorizations, and other aspects. Step 2240 is very unique in presentation as compared with prior products and will be detailed in a further section. In step 2250, reviewers may save comments on areas found to be of interest in either further evaluation and/or areas that appear similar enough to characteristics known of irregularity by skilled medical professionals. Comments in step 2250 would also save the particular aspect the medical professional is currently viewing, including, but not limited to zoom (magnification level), colorization or color enhancements, tilt or rotation, and any other configuration from the reviewer that would alter the visual image leading a medical professional to make an assessment of an abnormality. A reviewer of step 2250 may wish to have a specialist or second opinion on a comment and would then indicate this within the system, which then would trigger step 2260, an automated alert to another reviewer. An original reviewer may exit and re-enter a system in step 2240, 2250, or 2260 to view the results of said specialist review prior to moving to a finalization in step 2270.

A beginning of a report of findings is shown in step 2270, which is in part selection of previous comments from their own analyses, analyses by other medical professionals or review of specialists, and also automated analyses comments. A final report may or may not include all comments available, potentially only the most severe areas of abnormality might be of primary interest. Additionally, step 2270 may also save general comments as to the state of health of the patient, concerns or abnormalities not yet found but likely to occur in the future, and also abnormalities found and recommendations for future actions such as diet and/or treatments, and other items that would be obvious to medical professionals. Upon completion of the selection of comments, a final report can be recorded and printed into a patient file in the last step, step 2280. Electronic Medical Records (EMR) are currently in frequent use, and will likely be the repository of such reports, external to the system. However, an internal report logging history may be available from within the system without the need of EMR. Since in large part the report material is based upon quality images, it may be ideal to have paper/printed reports available from a remote service with quality printing ability, and is so included in embodiments of this invention in the combination of steps 2280 & 2290. After the completion of the final report, another opportunity for automated alerts is found in step 2290. Automated alerts expected from step 2290 would include an alert to schedule an appointment with the patient (with or without urgency), an indication to professional staff or service to print and file, a final report, and potentially alerts to fill out & submit therapeutic prescription or other medications, and other alerts that would be anticipated by medical professionals.

Scanned Image Creation

As one skilled in the art would recognize, a capsule being propelled by intestinal peristaltic action may produce scan data that may be captured in a forward or backward position axially as related to a previous scan data, the capsule may be tilting with reference to the axis, the capsule may be rotating about the axis, and the capsule may be adjacent to tissue and also separated from tissue at any point in time and within any scan. In addition, axial motion and acceleration are spurious, not consistent as is the case with traditional scanning mechanisms like flatbed scanners and satellite imagery. Thus, the general function of combining many pieces of scan data into one image is reasonably complex even though in some part it does exist in a specific environment in the combination of multiple satellite images into a single, larger image as displayed on the internet for services such as Google Earth and the like.

FIG. 23 depicts an embodiment model for creation of a single image from multiple scans taken over time and distance throughout the human gastro intestinal tract. This embodiment is based upon a scanning capsule as defined in U.S. Provisional Patent Application No. 61/030,453, filed Feb. 21, 2008 and entitled "Radial Scanner Imaging System," which is incorporated by reference herein in its entirety. Choice of a variety of different methods to produce a scanning capsule does not depart from the spirit and scope of this invention. FIG. 23 depicts image capture and processing that may occur on the capsule 104, the external computing device 108, or a device attached to network 504 such as remote entity 404. Selection of a particular device for a certain processing step is anticipated and inherent in a design for power consumption. Other selections of which device is used for processing does not depart from the spirit and scope of this invention.

In the embodiment of FIG. 23, a capsule starts by a single scan capture, as in step 2310. Several methods may be employed to determine when this scan is to happen, such as for example a detection of motion, an elapse of time, or a combination thereof. Such determination is not an object of this invention, but is described in U.S. Patent Application No. 61/030,453. A single scan, as would be anticipated, if in normal visual perception colorization (RGB), would require illumination methods as a light source is not present within the human gastro-intestinal tract. Such illumination is not an object of this invention other than to acknowledge its necessity, existence, and required control of the light source. A single scan, thus, would consist of an illumination and a capture. Capture is accomplished through an imaging device such as a CMOS or CCD device. In one embodiment, a special configuration of a standard imaging device such as CMOS or CCD device may be applied. In another embodied, scanned ultrasound images are captured by an array of PZT sensor elements.

An example of a side wall scanning capsule device is depicted in FIG. 24. An intestine 2410 projects its image, onto a cone shaped mirror 2412 which is angled and positioned to reflect the resultant image onto the imaging array 2414. A example scan, 2420, is shown as image 2422 upon array 2414. Referring back to FIG. 23, step 2310 refers to the capture of this image 2422 by a device 2414, which may or may not be rectangular and may or may not be fully populated with image cells. Additionally, then step 2320 is a process by which a ring image is stored in electronic elements such as memory cells, in which a depiction presented to a human would result in an isosceles trapezoid. In FIG. 24, the ring image 2422, with an arbitrary position 2424, results in an isosceles trapezoid strip which is a linear projection of the ring similar to a flat map of the otherwise ball shaped earth. In FIG. 24, the image manipulation process is shown as 2430, and the resultant trapezoid is depicted as 2435. Image 2435 is shown as an isosceles trapezoid for understanding only. Actual memory storage may be different, however, the distance around the inner ring of image 2422 is a shorter path than the outside ring and the differing sizes considered.

Referring back to FIG. 23, process step 2325 (also process 2440 in FIG. 24) converts this difference of path lengths for multiple lines (depiction trapezoid) and converts the lines to equal lengths in a resultant rectangular depiction 2445 in FIG. 24. Since the original capsule is propelled by the peristaltic action of a human, the capsule may rotate axially as well as tilt/yaw with respect to an axis of a proximal human intestine. FIG. 23 then depicts a process for manipulation of an image strip to adjust, or compensate for axial rotation (process 2330) and also tilt and yaw (process 2335). Additionally, as a larger, full image is being built, it may be appended in one direction by single scans. Since a human intestine on average moves from stomach to colon, the image is generally appended in this direction. However, well known to a gastro-enterologist, a human intestine will both propel forward (toward the colon) and backward (toward the stomach) a capsule at any given time, or scan. Thus, an additional process, 2340, would be used to essential invert a resultant single scan if a direction of movement is backward. Alternatively, step 2340 may discard completely reverse movement scans. It is important to note that step 2330, 2335, and 2340, also shown as 2450 in FIG. 24 are separated and ordered by way of example only. Steps 2330, 2335, and 2340 may be done in any order, or may also be combined into a single complex operation (2450) without departure from the spirit and scope of this invention. The resulting single scan of process steps through and including 2340 is depicted as 2455 in FIG. 24.

The single scan is now prepared to be merged with other such scans into a larger, full image; the process shown as a first step 2345, which determines at what specific location and rotation a single scan should be placed into the fuller image. In a simple merge, a new scan is just appended upon the end of the larger image with no overlap or adjustment. Typically, however, it is best to have some overlap of an image to determine exact merge points. Features present in images may not line up exactly, in which an additional process in the merge is employed to average out differences in features. A merge process could be as simple as an arithmetic average of a pixel in a larger image with a pixel in a single scanned image for all pixels in the single scanned image area. However, it is likely that a weighted averaging and other mathematical functions would be deployed in a merge of a larger, fall image and a smaller single scanned image. FIG. 23 shows the step 2350 as a merge process to include all varieties of merging functions and algorithms. FIG. 24 shows the merge process as step 2460 and the resultant depiction of the data as image 2465, a compilation of multiple merge processes of multiple single scanned images. The same process may be applied to scanned ultrasound images.

A compilation of images may be desired to be forwarded from a smaller device to a larger storage capacity device. In step 2360, a device may elect to forward a full image (compilation of multiple single scans). Reasons may vary widely depending upon a particular implementation. Some exemplary reasons would be time elapsed (to achieve a pseudo real time environment while also reducing image data transmitted), and also image buffer full, or a combination of both. If there is no reason to forward a compilation, then process returns to capturing a next single scan. However, if a full image is to be forwarded, then this image will be queued for transmission, prior to returning process flow to collect a next single image.

Image Display

Referring back to FIG. 22 and for review, a single image is available after step 2212. Auto analysis can be applied to this image in step 2214. This process can be repeated many times based upon timing, amount of image data collected, or other analyses to image and data received (such as location). Repeating the process in a very timely manner would result in a pseudo real time image update & availability. It is anticipated that a last scan, shown in step 2218, triggered by a last communication, an exit of the capsule from the body, a determination based upon auto analysis in step 2214, or other system applications and timers will make available a full and final image for an automated and medical professional review. Final automated analysis will occur in step 2220, and upon completion(s) will trigger a single or multiple alerts to a single or multiple persons or systems that the image and results of analysis are both complete and available, as is depicted in step 2230.

It is an object of embodiments of this invention to apply potentially many discrete automated processes selected either by medical professionals, general subscription profiles, or another method of pre-selection of automated processes. Each discrete automated process will analyze the image and produce results via comments with respect to a particular section (location & magnification), aspect, and colorization of the image. A future review by a medical professional will be able to view an abnormality at the image detail (location, zoom, aspect, colorization) that was selected as an abnormality of interest by an automated process. Embodiments of this invention anticipate automated processes individually or in combination drawing upon multiple image libraries of exemplary abnormalities to be evaluated for diagnosis, with confirmation by a medical professional. Furthermore, these image databases would contain multiple example images for each abnormality or pathology of interest. Automated processes then would compare images of a capsule endoscopy with multiple images of a library of abnormalities. The automated process would select a matching area (location, zoom, colorization, aspect) of the capsule endoscopy and comment upon the matched abnormality, the area (e.g., location, zoom, colorization, and aspect), and the likelihood of a match (percentage or other number system is anticipated).

Furthermore, it is an object of embodiments of this invention that there would be automated processes with computational imagery analysis for the generation of the location and likelihood of particular common sections of the gastro-intestinal tract, for example the beginning and end of a small bowel. Automated processes are anticipated to be constructed as: i) imagery analysis without image library comparison, ii) direct comparison with a particular image of a library with a current image of capsule endoscopy, and iii) imagery analysis by way of comparison between a current capsule endoscopy and a fully characterized and collective set of images composing an entire library of images. Use of any and/or all of the above methods of imagery analysis is anticipated and an object of embodiments of the present invention. Additionally, computational image analysis would allow for extraction from image data, three dimensional (3-D) views and "super-resolution". Scanned image data is ideally suited to apply computational analysis techniques that can't conveniently be achieved by conventional photography.

FIG. 22, step 2240 depicts another form of availability of an analysis by other reviewers of images prior to a primary medical professional review, in, the automated fashion of work flow management by way of alerts and availability of images for review. By way of example only, a primary care physician might pre-select a trusted gastro-enterologist and a trusted celiac disease specialist to review results of a patient's capsule endoscopy as soon as it is available for review. These trusted specialists may be of personal contact within a local community, but also anticipated is a service, or services, that offer remote reviewing professionals as a solicited service to the primary care physician. The latter service is similar in nature to a current x-ray process at some hospitals, whereby an x-ray, digitized, is transported electronically to reviewers often in India, and rapidly interpreted with results returned to the hospital. It is then anticipated that specialized services for the interpretation of capsule endoscopy images will be automatically preselected by a primary medical professional or staff thereof associated with a particular patient, and that the pre-selection of the service will occur prior to the analysis of the imagery by the same primary medical professional or staff thereof.

It is an object of embodiments of this invention to also afford the opportunity of an initial analysis of a capsule endoscopy imagery by a primary medical professional and then a subsequent electronic request of a service (new or past used) and a further alert system generation upon this referred service completion of analysis prior to the primary medical professional's report of finality, depicted in step 2280. Embodiments of the present invention are generally constructed to facilitate automated processing of capsule endoscopy imagery in a systematic and preselected method while also allowing a more time consuming and manual method to a primary medical professional on a case by case basis as is sometimes necessary for proper evaluation of non-typical patient symptoms and ailments. In step 2240, the selected additional (not primary) analysis conclusions are documented with respect to a patient's capsule endoscopy image. As is with the automated image analyses of step 2220, these analyses are in the form of comments with respect to a specific location, magnification, colorization, and aspect so as to afford a repeatable view to a primary medical professional with the results of the analyses. In step 2250, each of potentially many additional reviewers of the image save the results of their analyses with respect to the image. In step 2260, automated alerts, upon completion of each and all of the reviewers of steps 2240 & 2250, are sent to notify the primary medical professional that reviewers' comments are complete. A primary medical professional can then schedule his time or immediately start his own review as depicted in step 2270.

FIG. 22, step 2270, shows a process step for a primary medical professional to select a subset (one, many, or all) of comments within a superset of comments produced by self (step 2240), additional medical professionals (step 2240), and automated processes (step 2220), to be included in a final report. Once the comment selection has been made, the finalization of the report is completed through step 2280. A final record, albeit printed, electronic, or both is memorialized. A current typical procedure would be to print out the report to be filed into a patient record. However, in the last few years, Electronic Medical Records (EMR) have become more popular as technology in this area has expanded, matured, and become more reliable. Another service opportunity to a physician's office is available at this step, step 2280. The objective of embodiments of the present invention is to have the product of a high resolution imaging system and management thereof for a gastro-intestinal tract. Part of this system could be a high resolution printed report. Current Capsule Endoscopy systems do not provide for resilient, high quality printed images as a result of the low cost requirement on office co-located equipment for the medical professional staff. An objective of embodiments of the present invention is the system and method for producing a very low initial and residual cost of producing very high quality printed images and reports. In step 2280, the selection of a print service is an object of embodiments of this invention. A print service would acquire a high volume and high quality print equipment, and have access to the final report created from step 2270. In an embodiment, this remote, electronic system would trigger an automated printout, associated with general information about the medical professional and office, such as contact information, address, and optionally express mail account numbers and related information. In step 2280, office information, an automated print out of a report, plus a shipping document would facilitate minimal human involvement and reduced residual labor charges. An automated printing service with multiple clients could then produce very cost effectively extremely durable high quality image reproduction for permanent record storage, transporting this document back to the originator's office. And, finally, in step 2290, preconfigured alerts would be dispatched indicating that a final report is available. An example of such an alert would be to an internal office staff for scheduling a patient visit, or potentially an automated scheduling calendar would generate an electronic patient visit request sent directly to the patient's email, phone, or similar electronic device. Steps 2240 through 2280 are further discussed in the next sections.

Image Display System

FIG. 8 depicts a system 800 for displaying a plurality of different aspects of images captured by an ingestible scanning capsule. An operator, 810, interfaces with system 800 and controls position and aspects by interacting with various user interfaces, including but not limited to joystick 820 and keyboard 821. The interface devices are connected to a host computer 841. Host computer 841 displays information and/or an aspect 831 of a current selected position, as it collects information from devices (not shown) attached to network 802. Host computer 841 also directs slave computers 842 and 843 to display different aspects of the same location of the GI tract currently shown on the host computer. In an embodiment, each of slaves 842 and 843 have their own computing processor and directly attached monitor displaying aspects 832 and 833, respectively. In an embodiment, control from the host to slaves occurs across network 802 through network connections 851, 852, and 853. These network connections can be, industry standard connections, such as, for example, Ethernet, Wireless, or Cellular data networking, and other types of connections that will be apparent to those skilled in the art.

FIG. 9 depicts another embodiment of a display of multiple simultaneous aspects. A computer 941 is suitably selected to have sufficient processing power and memory to process and display multiple aspects. Operator 810, interfaces 820, 821, network 802, and network connection 851 are the same as shown in FIG. 8. Multiple monitors displaying aspects 831, 832, 833 are all connected to a same computer 241.

FIG. 10 depicts another embodiment of a display of multiple simultaneous aspects. A computer 1041, similar in nature to the computer 941 of FIG. 9 has only one display. However, aspects 1031, 1032, 1033 all appear in sub-sections of the full monitor. Operator 810, interfaces 820, 821, network 802, and network connection 851 are the same, as depicted in FIG. 8.

FIG. 11 illustrates a display 1100 as is similar to that of FIG. 10 having multiple aspects and controls on one display unit. A traditional endoscope aspect, referred to as looking down the tube is shown in area 1130. The dark spot shown as 1133 is a part of the GI tract too distant to be in focus or illuminated. The aspect of area 1130 shows very limited overall imaging. Traditional endoscopes and even the newer ingestible camera devices only provide this limited viewing picture. Diagnosing physicians are not impeded by this aspect with traditional endoscopes in that they have to take the time to navigate the endoscope so as not to puncture the GI tract in the patient, as this procedure is effectively real time with the imaging. However, in newer ingestible camera endoscopes this traditional aspect forces the diagnosing physician to weed through picture by picture almost one at a time to be able to get an overall view of a patient's GI tract. Image data collected by a scanning imager capsule provides an overall view that greatly enhances the use of a viewer's time. This aspect, is shown in area 1110, and depicts virtually the result of removal of the GI tract, stretching it into a straight line, cutting it open on that straight line, and folding it open. Since the GI tract of a human, for example, is very long with respect to its circumference, or width as would be folded open, the aspect shown in area 1110 shows multiple sections. For example, images of the mouth and throat would be on the left side of the top section. The right side of the top section and the left side of the middle section might show the beginning of the small bowel. The image through the small bowels may continue throughout the middle section and into the start of the lower section. The image data just prior to excretion would be located to the right of the last section. A person skilled in the art would realize that any number of sections could be used without departing from the spirit and scope of this invention.

Since an entire GI tract displayed, as is in area 1110, is very small compared to potential issue needing further investigation, it is conceived that only summary (low resolution) information would be displayed in area 1110. Judging from the summary images in area 1110, a specialist may want to zoom in to a higher resolution image. An area 1120 provides a close up image of an area of interest. This close up area is also displayed for reference as subsection 1111 of area 1110. A close up area 1120 has a known position with respect to the entire GI tract. Statistical data corresponding to this is shown in area 1160. Data that can be shown is total time from entry to exit of the GI tract, and similarly, a relative time from entry as well as a relative time to exit is also displayed. More useful, however, is distances. Since the ingestible scanning capsule can be located with precision an entire length of the GI tract, the distance from entry, and the distance to exit can be displayed for use by the diagnosing physician. Distances are extremely useful in determining which of other procedures would be appropriate. For example, if an area of interest were 20 inches from the mouth, a traditional endoscopy procedure starting from the mouth would be appropriate while a colonoscopy starting from the rectum would not be an appropriate procedure. Similarly, an area of interest 6 inches from the rectum would suggest the use of a colonoscopy over the endoscopy procedure that starts from the mouth. Since the area 1110 is a display based upon distance, a time display in area 1160 could indicate areas where peristaltic action is faster than or slower than some criteria indicating problems that need further investigation by the diagnosing physician.

A specific anomaly of the GI tract is depicted in the multiple aspects 1110, 1120, 1130 and in the location of the GI tract currently selected by the operator is shown with 1112, 1122, and 1132, respectively. An example of an anomaly would be a spot of blood. A person skilled in the art would recognize images of a multitude of anomalies. All anomalies can be shown on area 1110 as it depicts the entire travel through the GI tract. One such anomaly depicted is anomaly 1113. Anomaly 1113 is a color enhancement of a non-visual sensor and/or imager. Examples of anomaly 1113 would be high intensity reflections of UV, as is known for cancerous growths, high intensity reflections of IR indicative of a high volume of blood flow, detection of a concentration of heat indicative of cellular activity and/or infection, non-uniform reflectivity of ultrasonic waves in part indicative of dense, absorbing tissues such as polyps and other potential growths not found in typical tissues, and other such sensors. Controls that tarn on and off color enhancements as well as controls setting thresholds for sensors or imagers not in the visible light spectrum (not shown) would give an operator of the present invention a method to easily highlight for further evaluation (as in zoom in) certain areas of the GI tract. This process greatly eliminates the time necessary to accurately detect areas of concern within the GI tract of a patient.

An operator, 810, once determining an area of interest is allowed to annotate their findings in area 1150. The location within the GI tract, hence within the scanned data in combination with the ability to highlight, circle, or otherwise indicate a zoomed in area (such as storing the configuration of area 1120) is also stored, as an area of concern or finding as a distance into the GI tract, a radian angle and a zoom aspect. Additionally, the operator information and optionally qualifications (or index thereto) are also stored with the annotation of the area of concern. A person skilled in the art would realize a database of annotations with index into the scanned data at a certain point and operator database index could be an efficient mechanism to keep a record of the areas of concern for each individual use of an ingestible scanner. Once such an area of concern database is built, it can be very functionally utilized to skip around very quickly to just those areas that should be studied more closely or even reviewed with the patient. In an embodiment of the present invention, a report of selected or all areas of concern can be created from the annotations stored at the time of review, or at a later time or different computing platform remote or otherwise.

An embodiment of this present invention affords an opportunity for construction of an expert software system or autonomous graphical pattern recognition system to parse through a patient's scanned data and automatically generate areas of concern. On FIG. 11, such an expert system is demonstrated in area 1140, for example a "UV Reflective" category has been selected by operator 810. Such a selection is a filter to accept any area of concern information from an expert system, in this case, that recognizes certain scanned data from a UV emitted light source as being above a certain level of reflectivity and concentration that would potentially indicate a cancerous growth. In this invention, operator 810 has the ability to select which filters he or she is interested in observing for a particular patient. Once a selection or multiple selections are made, the operator can utilize controls 1145 to skip forward or backward through the index of areas of concern. It is important to recognize that both expert systems and also specific human reviewing authorities (diagnosing physicians, specialists, etc) are given as filter criteria allowing an operator to select specific historically accurate resources for a patient's current health issue or concern. In the aspect shown in FIG. 11, area 1110, for example, there are two areas of concern selected by filters for UV and Dr. Peters. The current area of concern shown relates to Dr. Peters and is also indicated in area 1150 showing the diagnosing physician's annotation of the area previously reviewed. The operator can select a next area of concern skip function by clicking controls 1145. The next area of concern, as indicated by 1113 would then be displayed with different aspects in areas 1120 and 1130. Alternatively, the controls 1145 may be located or duplicated as specific buttons on joystick 820, or specific keys on keyboard 821, and so on as would be anticipated by a person skilled in the art. There are two areas of concern demonstrated in area 1110 but are not included in the skip function as the resource was not selected in area 1140, as indicated by several sources not having a selection icon matching the name of the source.

An operator, such as person 810 in FIG. 8, is able to navigate the aspects of areas 1110, 1120, and 1130 in a number of ways. A linear movement, as would be the case with pushing and pulling a standard endoscope (i.e. up and down the tube), is controlled with either the joystick 820 of FIG. 8, the keyboard 821 of FIG. 8, or a mouse click on control icons 1135 of area 1130. Additionally, the operator may use controls 1145 or a duplicate set connected with buttons on joystick 820, to skip directly to areas of concern. It is also anticipated by this present invention to afford controls for zoom and rotation for areas 1120 and 1130, such as might be a left and right twist of a joystick and a straight left and right joystick manipulation for zoom and rotation, respectively.

An ingestible scanning capsule stores very specific location data with each scanned image data. Location data is computed with reference to a fixed point, typically reference to a location of a belly button of a human subject as a permanent point of reference. An objective of the present invention is to be able to display a path of travel over the duration of time an ingestible device passes through a GI tract.

FIG. 12 depicts a normalized graphic of a typical human subject 1210, with an exemplary GI tract 1220, and an exemplary travel path 1230 of an object that might pass through the human subject. FIG. 12 is for reference as a point of demonstration of the present invention.

In an embodiment of the present invention, an additional aspect of display for display 1100 (or additional monitors as depicted in FIGS. 8, 9, and 10) is explained with reference to FIG. 13.

FIG. 13 schematically shows a normalized depiction of a human 1310 for a background reference. A total traveled tract 1320 is computed and overlaid upon the background. A current location or area of concern is chosen for display on multiple aspects and is graphically represented by a control and icon 1330, control 1355 and control 1365. Control 1355 depicts a linear progression in distance from mouth (or first acquired location) to anus (or last acquired location). Control 1365 depicts a linear progression in time from ingestion (top) to excretion (bottom). Software allows movement of the controls 1355 and 1365 only up and down—for example by clicking a mouse and dragging the control up or down. Control 1330 is more complicated, in that 3 directional display and movement can be accomplished. In an embodiment of the present invention, a mouse drag on a 2 dimensional (x, y) level can move the control/icon 1330 around the background 1310. When the control is released (for example release of the mouse button), the control/icon 1330 is placed upon the closest point of the path 1320. To achieve a 3 dimensional control, a rotation control will spin the entirety of 1310, 1320, and 1330 as it was on an axis from top to bottom and in the center of the body.

An additional spin control could optionally be added to the aspect of FIG. 13. Alternatively, a joystick 820 twist control could accomplish the same spin function. In an alternate embodiment, areas of concern can be denoted by icons placed upon the travel path 1320 as would be considered by persons skilled in the art. An operator may quickly determine what additional procedures may be needed by a quick glance at a distance indicated by control 1355, which graphically and simultaneously depicts distance from entry to area of concern and also distance from excretion to area of concern. A diagnosing physician could then easily tell if an endoscopy or colonoscopy follow-on procedure would be appropriate.

FIG. 14 schematically shows the functionality of display of a path, and area of concern directly upon a patient. An area of concern may generate a request for additional procedures such as ultrasound analysis, MRI imaging, X-ray imaging, or even exploratory and other types of surgical procedures. All of the above can benefit from time savings, cost savings, and reduced impact upon the patients impact from a surgical incision size and/or prep area. A projection of path 1320 and areas of concern 1330 from FIG. 13 is demonstrated as path 1420 and areas of concern 1430, respectively in FIG. 14. The projection device may be as simple as a typical office projector as would be typically be utilized for meeting presentations. Other devices could be utilized without departing from the spirit and scope of this present invention. As described earlier, a fixed point of reference, for example belly button 1415 is stored with the location information of the path 1420. A first procedure would be to align the projection so as to fit the indication of belly button 1415 with the patient's actual belly button. A second procedure would include any necessary rotation to align entry (mouth) and exit (anus) of the tract 1420 projection so as to align to the patient 1410 without rotation off axis. A third procedure would be to size the display to fit the proportions of the patient 1410. A zoom in & out control (not shown) or a physical movement of the projection device towards and away from the patient will be performed until the entry point 1440 and the excretion point 1450 of the tract 1420 match the patient's physical location of mouth and anus. Referencing FIG. 11, a skip from area of concern, to a next or previous area of concern will illuminate an area of patient with icon 1430. The icon may be utilized directly to capture data from another procedure. Additionally, the icon 1430 may be utilized indirectly by further marking upon the patient the index or other indication of the area of concern for procedures to take place at a later time or in another facility or room.

FIG. 15 is a flow chart of a main processing system of image processing software for rendering the multiple aspects and views as depicted in FIG. 11, according to an embodiment of the present invention. By way of example only, FIG. 15 flowchart shows a loop function. As is typical with a loop function in a display scenario is an initialization phase as shown with steps 1502-1504, a graphical drawing function or functions shown with steps 1510-1530, a control or input and processing of the input as shown with steps 1540 through 1571, and loop control returned back to graphical updates in step 1530.

At step 1502 the main processing routine is initialized specifying in part a first position, colorization, and magnification level, the first position at the start of a full image available from a series of single scans, the result of processes shown in FIG. 22. At step 1504 all filters are turned off Filters can be selected by an operator of the software to include or exclude numerous comments on abnormalities found by the person or process, or groups thereof, that have placed comments upon the full image of a particular gastro-intestinal scan of a patient. For example, pre-selected automated analyses processes for celiac detection may afford a reviewer an opportunity to initially quickly select the automated processes, or more specifically a trusted celiac finder automated process and skip (see FIG. 11, item 1145) directly to an area of interest with a suspected abnormality such as celiac disease. Similarly, in another example within embodiments of the present invention, a pre-selected trusted reviewing, entity, employing human labor potentially in a low labor rate country such as India, may have pre-viewed the scanned image, made comments on certain portions of the image, and completed their independent analysis for a primary reviewer/doctor to initially and quickly select their findings and jump to the view indicating, for example, an area of discolorization abnormality indicating a suspected irritable bowel disease.

FIG. 15, steps 1510 and 1520 initialize a graphic display or background and are explained further in a following section. The initializations of 1510 and 1520 will provide a display for substantially non changing portions of materials on the displays as a reviewer starts to view a capsule endoscopy scanned image. Step 1530 is also defined in detail in following sections and FIGS. Step 1530 updates non static graphical information, for example areas 1120 and 1130 in FIG. 11, and also when moving through a magnified image from an overall single scanned image of a patient's gastro-intestinal tract. After the system and displays have been initialized, user input for navigation and commentary is accepted as is depicted in step 1540. Depending upon the type of input, as determined with steps 1541 to 1549, algorithms are deployed in steps 1561 through 1571, and loop control is returned to update the display(s) in step 1530 as would be appropriate. Step 1541 affords a reviewer an ability to select and deselect a variety of comments to review from other reviewers and/or automated processes. If a selection is made, a corresponding action 1561 toggles a specific filter on or off as requested by the reviewer.

Once the selection is made, control is passed back to the input loop in step 1540. Step 1542 affords a reviewer its own opportunity to save a current viewing magnification level, colorization, and position along with a comment about a specific area and a potential for an abnormality. Step 1562 saves in a multitude of indexes and databases the information of the comment as well as the other information about the current view, location, magnification level, colorization, etc. It is important to note that, while the current FIG. 15 demonstrates a textual comment, it is by example only Embodiments of the current invention also anticipate the use of video commentary, audio commentary, and also chalk talk style overwriting of shapes and freestyle drawing (of a variety of colors) for the commentary of a particular graphical image. Examples of each are not included for conservation of text length, but are anticipated by this invention.

Step 1563, 1564 affords the reviewer in a current magnification level (zoom level) to scroll forward and reverse, respectively, with respect to the fall gastro-intestinal image and, for example, forward being to the right, and reverse being toward the left. Additionally, a movement may be defined as being a percentage of the current magnified view, such as 50% (half of the image remains on the magnified view as a new image is displayed). Embodiments of this invention anticipate several methods of image movement—i) a more simple form of movement which is to re-draw a new image, ii) move a portion of an image on the display without reference to a full image file while accessing that file for only a new portion of the overall magnified image to display, and iii) a more visually soothing smooth scroll of an image by continually redrawing the image only a few percent of change, for example 25 times redrawing an image moved only 2% in a certain direction. The latter smooth method, although more technically difficult, is certainly more soothing to the human eye and brain, and likely worth more to a typical reviewer of a multitude of images frequently. The program updates the new location center, magnification level, colorization, etc as appropriate for user input, then passes loop control back to step 1530 to perform the update of displayed information from a new aspect, and then on to step 1540 for new user input.

Step 1545, 1546 accepts input from a reviewer to launch a timed step forward and reverse, respectively, without the need for additional consecutive inputs by a reviewer. Effectively, then, steps 1545 and 1546 advance a magnified image forward and reverse such as with steps 1543 and 1544 respectively and further updated images from steps 1563, 1564, respectively, and then back to 1530. This advance is a repetitive advance initiated by a single user input and continued until either, i) the end or beginning of the full image (respectively) is reached, or until an additional input from a reviewer is received. The additional input of this example might be a second input, such as is with a toggle, of the initial input, such as a first FFwd initiates a forward continual movement, and a second FFwd terminates the forward continual movement. In an alternate embodiment, not shown but inclusive in this invention, a first FFwd would initiate a slow, continual movement forward, a second FFwd would initiate a medium speed movement forward, and a third FFwd would initiate a fast speed movement forward through the full image. An object of this alternate embodiment would be a termination of the movement forward by either a user input of a PAUSE function (not shown), and/or a selection of any other movement inputs such as the forward, reverse, FRev, Comment, Filter Selection, and so on. Still further, a typical keyboard (FIGS. 8 & 9, item 821) 'Esc' or <space> or other typical keys are an anticipated movement termination user inputs. Steps 1545 and 1546 call upon the functions 1565 and 1566, respectively, to update a location, continually and autonomously, while returning loop control back to update of the display image(s) in step 1530 and additional user inputs in step 1540.

Step 1547 affords a reviewer of an image and its corresponding, magnification level a direct jump to a specific location within the full image. An example of a typical implementation would be a mouse click on the full image, while this input would display an additional magnified view of this location upon another aspect. The location is selected, optionally selecting a default magnification level, as a part of process 1567, and then returning, loop control back to updating displays with step 1530.

Steps 1548 and 1549 correspond to a reviewer's request to jump to a pre-defined location, magnification level, and colorization as stored and indicated in a previously commented step. Furthermore, the sequential stepping through of comments are available, but only for those comments by reviewers and/or automated processes that have specifically, or by group, selected through the filter selections of steps 1541 and 1561 by the current reviewer. It is anticipated that an embodiment of this invention would allow a configuration, not part of this specific procedure FIG. 15, to pre-select a certain common set of filters, customizable to any specific reviewer as part of a login procedure. Since these comments in this embodiment are considered to be a list which secondarily then can index a location within a specific full image, two steps may be performed, such as 1568 which selects a next comment from a list of comments, and subsequently step 1570 which selects and sets a specific location (magnification, and colorization) from attributes of a present comment prior to returning loop control to steps 1530, updating the displays, and 1540 for getting a next user input.

FIG. 16 is a flow chart of a subroutine of the image processing software for rendering a linear aspect of the displays depicted in FIG. 11, according to an embodiment of the present invention. FIG. 16 is also a more detailed expansion of the step 1510 of FIG. 15. FIG. 16 is provided as an example of an optional routine to render a single image (without respect to scrolling within a window) from multiple individual pieces of that image, called frames, from a storage unit rendered upon request real time or pseudo-real time from a reviewer of the full image. Optionally, FIG. 16 could be implemented upon image acquisition or batch mode during, an overall image acquisition process and stored as a full image for later real-time viewing. However, FIG. 16 will overall appropriately fit a full image, possibly scrolled, into an available display space commonly referred as a 'window'. FIG. 16 is one example of a method to display a full image into an available display space. Other implementations do not depart from the spirit and scope of this present invention.

Step 1610 of FIG. 16 demonstrates an initial opening of an image based data file containing a multitude of scanned images comprising in total a full scanned image of a gastro-intestinal tract. It is implied that these individual frames may, but may not contain duplicative information between adjacent frames. Step 1612 calculates, from information within the image database, a total quantity of frames contained within the full available image. Step 1616 calculates the number of available pixels in the current available display space from, for example, interrogation of the operating system under which this procedure is currently miming. Step 1618 calculates from the preceding information a number of frames that will need to be compressed into a single row or column of pixels based on the uniform distribution of image data across a non equal number of pixels available to display the image within. Step 1620 is an initialization of a loop to then render the fall image across an available display.

Step 1630 initiates a loop of sections. A full contiguous image of a gastro-intestinal tract is assumed to be long with respect to the width, if each pixel of data is square—or non-distorted in an x and y direction. Effectively, for demonstration, if a gastro-intestinal tract would be removed from a patient, cut and splayed open so as to provide a flat surface, it would be approximately 300 inches long while only 3 inches wide. In order to fit this object into a more square display area, it would be ideal to evenly divide these 900 square inches into a say, 30 inch by 30 inch area. More specifically, a full 300 by 3 inch image should be sectionalized into 10 of 30 horizontal by 3 vertical inch sections, that would be then horizontally stacked one upon the other. While this is an ideal sectionalization for example, it is anticipated by embodiments of this invention to also have spacing, rulers, and other text and graphics to be applied within the overall display window for best viewing as would be determined by an expert in graphical user interfaces (GUIs). For purpose of simplicity, these details are intentionally left out of the example, but are implied within the spirit and scope of this present invention.

So, step 1630 has calculated an appropriate number of sections to display, and initially sets up for display of a first of potentially many sections. Step 1640 initializes a loop controlling where in the graphical display a current rendering of a row of image data should be drawn. Step 1650 then moves through the image data, step 1652 collects into the program memory that image data, step 1654 compresses or expands as necessary frame pixels to display pixels, for example averaging a multitude of image data pixels to substantially less display pixels. Step 1656 simply loops back to step 1650 to get all frames available for a particular column for display. Step 1649 as shown both displays (renders) the results of 1650 through 1656 onto the display/window, then advances to the next column, p, of the display by looping back to step 1640. Step 1639 similarly advances to a next section to display in the window, and returns loop control back to step 1630 for a next section. When all sections have been rendered onto the display, program exits from step 1639.

FIG. 17 is a flow chart of a subroutine of image processing software for rendering a drawing of the full GI tract in 2D as is shown in FIG. 13, according to an embodiment of the present invention. This embodiment of the present invention assumes a reasonable accuracy of location within the image acquisition system. One embodiment of such a system would be an acoustic data transmission system. Such a system with accurate location ability is defined in publication WO2008-030481-A2, incorporated by reference herein in its entirety. In such a system for periodically gathering image data, as a result also location information is stored within the data. Embodiments of the present invention refer to this data storage as a frame database. However, a storage of location information with image data based upon a real human subject is not necessarily nor frequently of the same dimensions as an output display. Hence, a translation, or resizing of the location, and potentially normalization and stabilization of the location information, may be necessary and an object of this routine shown in FIG. 17.

Step 1710 opens an associated image file, or frame database. A first and last entry of location information, for example, would indicate entry (mouth) and exit (anus) locations of the body as would be the case with a location based upon acoustic location systems. However, additional information, such as signal attenuation, would be likely used in an RF based location system, as an example of an alternate embodiment of a storage of location within the body of a specific image acquisition. Step 1712, nonetheless, finds a entry and exit location information. Step 1714 renders a standard picture, a generic drawing, or optionally an actual picture of a human subject. Step 1716 stores a defined maximum space available for the display. Step 1718, then, with size information from an available display and an available location parameters from a gastro-intestinal transit, computes a ratio so to fit the location information from the transit onto the static painted image on the display. Starting back from the top of the image data base with a first location, a loop is setup with step 1720 (first record start), and 1722 (a computation of an absolute pixel location from a relative base of locations stored within or as an index to the image database. Step 1730 depicts a start of a loop that reads locations with times of signal detection (relative to ingestion and/or absolute time reference). Step 1731 gets a database entry and related records in other associated databases, for example location and time references. Step 1732 stores, in 3 dimensional representation, a path from a previous database entry to this current database entry and in addition accumulates a distance traveled as a path length, or a conversion from 3 dimensional travel to a 1 dimensional top to bottom reference. Step 1733 stores a relative time offset from a first and last time available for this path. Step 1734 applies a ratio to this path, and applies this in step 1735 when rendering a path (line) onto the display/window. When all records have been evaluated, loop exits at step 1739. Step 1740 draws a distance bar background graphic with the accumulated total distance traveled from step 1732. Step 1750 textually depicts on the display/window the beginning and final points on the background bar from step 1740. The distance bar graphic and textual information is as seen in FIG. 13, items 1350 & 1355. Similarly, step 1760 and 1770 draw another graphic bar and corresponding textual references, this time on the basis of time, as opposed to distances of 1740 & 1750. Steps 1760 & 1770 correspond to items 1360 & 1365 on FIG. 13.

FIG. 18 is a flow chart of subroutines of image processing software for updating multiple aspects of the displays and providing annotations as depicted in FIG. 11, according to an embodiment of the present invention. Step 1530 of FIG. 15 is a general title for a set of routines for a variety of aspects of a selected position within a full image of a gastro-intestinal tract made by, for example, an embodiment of a scanning capsule endoscopy product. Step 1530 includes a multitude of subroutines for a multitude of aspects. These subroutines are intended to be able to reside within one processing environment and also be able to be split into multiple processors. Additional aspects of a full display system are likely. FIG. 18 demonstrates by example only. Additional aspects or removal of aspects from the details of FIG. 18 does not depart from the spirit and scope of this present invention.

FIG. 19 illustrates flow charts of subroutines of the image processing software for updating a tract aspect and updating time and distance, respectively, of the displays depicted in FIG. 11, according to embodiments of the present invention. FIG. 19 is a further detail of step 1830 and step 1850 of FIG. 18. Step 1830, as described in FIG. 18, updates a tract display of FIG. 13. As shown, FIG. 13 is a 2 dimensional representation of a 3 dimensional tract taken by a scanning capsule endoscope, for example, over the course of an exemplary traversal of the capsule over time while in communication with an external receiver. As a human operator of embodiments of the present invention moves around an image of the gastro-intestinal tract by a variety of methods, the tract aspect will need to show a corresponding updated display of the current position of the current selected position. Step 1910 then is the beginning of the procedure to update the tract display. Firstly a procedure removes old, non valid information such as the cursor/crosshair, such as depicted as item 1330 on FIG. 13. Step 1912 re-computes a new position of the cursor. A desired position within the full GI tract is available from the system, and a correlated position with respect to a current ratio for display of the GI tract, is then computed. This computational result is used in step 1914 to redraw a current position indicative cursor on a 2D representation of a 3D GI tract. Similarly, step 1916, 1918 and 1920 removes, recalculates, and redraws, respectively, a indicator of position within the full length of the GI tract as is represented by item 1355 in FIG. 13. Additionally, and similarly, steps 1922, 1924, and 1926 will remove, recomputed, and redraw, respectively, an indicator of time elapsed from swallowing a capsule to reach a current position that is in view in a magnified view. Steps 1910 through 1926 offer by way of example only an update to three cursors/indicators. A person skilled in the arts may elect to have only one, two, all, or supplement information with additional information relative to information stored in the position and full image database(s) without departing from the spirit and scope of this present invention.

FIG. 19 additionally demonstrates a detailed procedure 1850 to update a time and distance display associated with a current magnification view of a full GI tract as exemplified by FIG. 11, items 1120 and 1110 respectively. Steps 1950 utilizes a user requested position from input while viewing a primary aspect, and calculates a distance from a starting point for a full length of a gastro-intestinal tract as is displayed on item 1110. The distance computed may be represented in a number of units, for example, inches, centimeters, etc, but would indicate a real position of the capsule that captured the image data currently viewed, as opposed to a distance on screen. Additionally, in an alternate embodiment, a scale of units would appear next to either a fall GI tract (item 1110), or a magnified portion of that tract (item 1120), or both so that visual objects could be visually sized quickly and without much error on the part of a human operator. In this alternate embodiment, a user requested change of a magnification level would also instill a change, and re-drawing of the previously discussed scale upon the magnified image 1120.

Furthermore, in another embodiment, a distance from a starting point may be selected as a first location (mouth), but it is also anticipated that a first part, for example image data from mouth to first part of small bowel, and a last part, for example image data of a colon and anus, of the full image, and operations within may be limited to a designated first and last position as a subset within the full image, to compute a starting position, a current position, and an ending position as represented in item 1160 of FIG. 11. Returning to FIG. 19, steps 1950, 1952, 1954, 1958, 1960, and 1962 calculate real distances that are traveled by a scanning capsule endoscope with respect to a start and end position that can be either a first and last position entry, or optionally defined as a subset, such as a first image data and last image data of a small bowel, a small and large bowel, etc. The optional definition may be selected by a human operator or also an automated process through image or colorization recognition algorithm, or a combination of the two. Step 1952 computes a real traveled distance from a current magnified view as selected by a user to the end position as just defined. Step 1954 formats the information of starting distance, distance of current position from start, distance of current position to end, and total end position, or length of capsule traversal. Step 1956 displays the formatted position in an aspect and as depicted as item 1160 of FIG. 11. Additionally, steps 1958, 1960, and 1962 compute and format times of transit with respect to the corresponding distances of 1950, 1952, and 1954, respectively. Step 1964 displays updated time of transit information in an aspect depicted as item 1160 of FIG. 11.

FIG. 20 is a flow chart of a subroutine of image processing software for updating a zoom aspect, according to an embodiment of the present invention. A full gastro intestinal tract display of FIG. 11 is shown as item 1110. As a user of embodiments of this present invention navigates around this full image, a window of a current magnified version is shown as item 1111 as a subset of item 1110. Item 1111 is shown to be a subset width, but a full height and is for example and simplicity only. It is anticipated and an embodiment of this present invention that a subset height and width for item 1111 is achievable by a reviewer's manipulation of inputs to the system. A subset image, then, can be enlarged and is shown in FIG. 11 as item 1120. As demonstrated, an abnormality of item 1112 in the full image is also enlarged and shown as item 1122 at the same magnification level as requested by a reviewer's input. The item 1120 is updated, or re-drawn through the procedure of FIG. 20. Step 2010 and 2012 retrieve two important variables and are a result of reviewer input—a current magnification (zoom) level, and a current location with respect to a full gastro intestinal image, respectively. User input for control of these two variables is anticipated to be similar to a well known user interface—a Google maps system. For example, to increase a magnification level, a user could scroll a mouse wheel. An additional example, a user could click on a position within item 1110 and skip directly to area at a currently stored magnification level. However, as an additional method of image manipulation that is not typical with a Google map type of application, is a user request to move to a previously commented material stored in association with a current full gastro intestinal image. A comment could be selected from, for example, a mouse click on a line of text in item 1150 of FIG. 11. Alternatively, a page up or down key could also, for example, move through previously commented material. Selection of a comment would move a zoom indicator, item 1111, and a zoom display, item 1120 to a specific location, a specific magnification level (stored with the comment), and other previously stored configurations such as colorization, brightness, color enhancements, etc. Although these additional stored configurations are not shown on FIG. 20 for simplicity, use of additional stored configurations of a graphical image does not depart from the spirit and scope of this present invention.

Steps 2014 and 2016 gather and calculate information about the size of the display area. Step 2018 and 2020 then calculate a ratio of how many pixels in an image database to translate onto a certain number of display pixels. As would be anticipated, a compression or an expansion on a pixel basis could occur, depending upon the display size for the magnified version, and the zoom, or magnification level requested by an operator of the system. Step 2022 opens an image database, and is optional. In some configurations, a software may already have the image database opened. In alternate embodiments where a zoom aspect is operating on a separate hardware system, the image database may need to be opened, or reopened upon an update of location and magnification level. Step 2030 begins a loop of rendering a line of graphical information, which is rendered after gathering all information in step 2039, also step 2039 increments to a next line until all lines required to update the display have been rendered. Step 2040 begins a loop of image data accumulation within the outer line loop of steps 2030 & 2039. Steps 2040, 2042, and 2049 acquires and manipulates image data from a database, a subset at a time—for example a frame of image data at a time. On, for example, a low magnification level request, many frames of an image database may be averaged together to form a single line of a display of the data. Alternatively, a large display may require the software to expand a single frame of data onto multiple lines of the display. So, step 2040 sets up a loop for multiple image data frames from a database, step 2042 retrieves the data from the database for a particular frame, and step 2049 compresses or expands the data as appropriate. One embodiment would compress image data by way of mathematical averaging of multiple pixels of information into one representative pixel. An alternate embodiment may deploy more advanced algorithms rather than a simple mathematical average. Such advanced algorithms are well know to those skilled in the art and their use does not depart from the spirit and scope of this present invention. Step 2049, in addition, will increment to a next, image data frame, if available and if necessary.

FIG. 21 is a flow chart of subroutines of image processing software for updating a tube aspect, according to an embodiment of the present invention. The tube aspect is depicted in FIG. 11 as item 1130. A complete, single, and full image of a gastro intestinal tract as in item 1110 is displayed as would be imaged in a topographical view. The current products in capsule endoscopy provide a typical endoscopy view to a reviewer, which is a camera view point in a gastro-intestinal tract, or tube, pointed and focused in an axial direction. Embodiments of the scanning capsule endoscope described herein do not offer directly this camera view point. Thus, to be compatible with an existing reviewer expectation, or backward compatible for viewing comfort, it may be necessary to provide this tube aspect. Since the image does not directly exist as a result of an imager output, it must be created. FIG. 21 demonstrates a simplistic embodiment of an algorithm that will render an axial view from an otherwise non-axially collected image data. Numerous algorithms are in place to render a different viewing angle from an otherwise initial set of image data, mostly in military applications. For example, public war time satellite imagery of ground terrain has been demonstrated to be viewed from a viewpoint of a virtual airplane flying close to the terrain through software data manipulation. Less viewed but still publicly demonstrated of recent years is in the world of sports. During the Olympics, several cameras tracked snow boarders going down terrain, and a virtual 3-D viewing angle capability was demonstrated and again in software manipulated image data to extrapolate from multiple actual images what an image would appear like if viewed from an angle that was virtual. A similar, but not identical process could be applied to a scanning capsule image data to render a scanning data collected on a pill surface as if it were viewed by a camera looking in an axial direction.

Firstly, in step 2110 and 2112 a procedure collects the center and size, respectively, of an area for display, such as in FIG. 11 item 1130. Step 2116 opens a scanned image database containing frames of image data. Step 2118 collects a current location as directed by a human operator, or reviewer, of embodiments this invention. Step 2120 creates an image array subset from a full image available in the database. The image array will have a starting point at the location indicated by the human operator, and an ending point at a defined point either forward or reverse into the database, the direction indicated by a direction of movement as directed by the human operator. Step 2130 through 2139 then mathematically manipulates the 2D scanned data subset array into another array that is organized circularly and subsequently renders the circular image data onto the tube aspect display window. Step 2130 initiates a loop of circles from outside, to inside, for example. Step 2132 retrieves scanned, linear image data and then in step 2134 mathematically fits a linear row to a circle of a single pixel depth, for example curving a line of image around a circle of a certain radius. Step 2136 stores the circular image information computed from step 2134. The process continues back to step 2130 for successive linear rows of information.

All rows of scanned image data have the same row size in pixels. However, in a circular representation, the number of pixels in a row of an outside radius is more than a number of pixels in an inside radius. Therefore, in step 2134, it is implied that the translation will be compressing linear rows of information into lesser pixels in order to be able to fit all of the information into a lesser radius circle. Steps 2130 through 2139 then convert an x,y image data presentation into a row, theta image presentation. FIG. 21 is a simple embodiment of the invention. A person skilled in the art would recognize that depth information, feature size, etc can be derived from the scanned image data to be able to render 3 dimensional information, such as a height of an abnormality, such as a polyp, for example from scanned information such as shading and linear depth of shade. This alternate embodiment, although more difficult to produce and illustrate on drawings, is both anticipated and does not depart from the spirit and scope of this present invention.

FIG. 22 is a flow chart of an overall scanned image collection, processing, and reporting system, according to an embodiment of the present invention.

FIG. 23 is a detailed flow chart of a scanned image creation process, according to an embodiment of the present invention.

FIG. 24 is an exemplary depiction of scanned data corresponding to the FIG. 23 process.

In an embodiment of the present invention, a report of selected or all areas of concern can be created from the annotations Illumination Although the embodiments described above have been described with respect to some sort of light illumination, the GI tract can be illuminated by various types of sources including white light, multi-spectrum light, narrow spectrum light, infra-red, ultra-violet, and even non-light energies such as, for example, acoustical energy, etc. The type of sensors used to image a scan can be varied as appropriate based on the illumination/sensor combination desired.

CONCLUSION

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. An apparatus for displaying, a representation of a gastro intestinal (GI) tract of an animal, the apparatus comprising:
    a memory that stores a plurality of annular images corresponding to a plurality of portions of the GI tract as an ingestible imaging pill passes through the GI tract;
    a processor configured to convert the plurality of annular images to a plurality of rectilinear images and to merge a first image from among the plurality of annular images and a second image from among the plurality of annular images to provide a composite image,
    wherein the processor is further configured to apply the merge process only to a first region of the first image that overlaps a second region of the second image to average out differences between the first and the second regions.

2. The apparatus of claim 1, wherein each rectilinear image from among the plurality of rectilinear images forms a substantially linear projection of the GI tract.

3. The apparatus of claim 2, wherein the processor is further configured to dynamically display the substantially linear projection of the GI tract in a manner dictated by a human operator.

4. The apparatus of claim 1, wherein the processor is further configured to permit a human operator to input a comment related to a portion of the GI tract in the composite image.

5. The apparatus of claim 1, wherein the processor is further configured to cause graphical user interface (GUI) controls to be displayed that are manipulated by a human operator to change a display of the composite image so as to focus on a particular feature of the GI tract.

6. The apparatus of claim 1, wherein the plurality of rectilinear images comprises a plurality of trapezoidal images, and
    wherein the processor is further configured to convert the plurality of trapezoidal images to a plurality of rectangular images.

7. The apparatus of claim 1, wherein the memory further stores specific location information with respect to a reference point for the plurality of annular images corresponding to the plurality of portions of the GI tract.

8. A method for displaying a representation of a gastro intestinal (GI) tract of an animal, the method comprising:
    storing, by an image display system, a plurality of annular images corresponding to a plurality of portions of the GI tract as an ingestible imaging pill passes through the GI tract;
    converting the plurality of annular images to a plurality of rectilinear images;
    merging, by the image display system, a first image from among the plurality of rectilinear images and a second image from among the plurality of rectilinear images to provide a composite image, the merging comprising:
    applying the merge process only to a first region of the first image that overlaps a second region of the second image to average out differences between the first and the second regions.

9. The method of claim 8, wherein each rectilinear image from among the plurality of rectilinear images forms a substantially linear projection of the GI tract.

10. The method of claim 9, further comprising:
    dynamically displaying, by the image display system, the substantially linear projection of the GI tract in a manner dictated by a human operator.

11. The method of claim 8, further comprising:
permitting, by the image display system, a human operator to input a comment related to a portion of the GI tract in the composite image.

12. The method of claim 8, further comprising:
causing, by the image display system, graphical user interface (GUI) controls to be displayed that are manipulated by a human operator to change a display of the composite image so as to focus on a particular feature of the GI tract.

13. The method of claim 8, wherein the converting comprises:
converting the plurality of annular images to a plurality of trapezoidal images; and
converting the plurality of trapezoidal images to a plurality of rectangular images.

14. The method of claim 8, wherein the storing comprises:
storing specific location information with respect to a reference point for the plurality of annular images corresponding to the plurality of portions of the GI tract.

* * * * *